United States Patent [19]
Kornbluth

[11] Patent Number: 5,665,588
[45] Date of Patent: Sep. 9, 1997

[54] DNA ENCODING NATURAL KILLER LYTIC ASSOCIATED PROTEIN

[76] Inventor: Jackie Kornbluth, 174 Pebble Beach Dr., Little Rock, Ark. 72212

[21] Appl. No.: 398,008

[22] Filed: Mar. 2, 1995

Related U.S. Application Data

[63] Continuation-in-part of Ser. No. 126,501, Sep. 24, 1993, abandoned.

[51] Int. Cl.$^6$ .............................. C12N 15/00; C12N 5/00; C07H 21/04
[52] U.S. Cl. .................. 435/348; 435/172.5; 435/320.5; 435/325; 435/252.33; 435/372; 536/23.1; 536/23.5
[58] Field of Search .................................. 536/23.1, 23.5, 536/24.5; 435/172.3, 240.1, 320.1

*Primary Examiner*—Suzanne E. Ziska

[57] ABSTRACT

A unique gene sequence encoding a natural killer lytic associated molecule (natural killerlytic associated protein) has been isolated. Using recombinant DNA techniques, the natural killerlyric associated protein may be produced in useful quantities. Methods for preparing the gene sequence and the gene product are disclosed, as well as methods of using the product to enhance anti-tumor, anti-viral and anti-microbial activity of natural killer cells. A method of inhibiting expression of the gene product is also disclosed, which may be used to turn off immune responses in situations of graft rejection and autoimmune disorders. Furthermore, methods of treating tumors and viruses in humans have been developed.

9 Claims, 18 Drawing Sheets

```
                10                      30                      50
       CGCCTGCGCAGGGCAGCGGCCCGCGGGGCGGAGGCTTTATAATCACTTCGTCGTTGCCGC 70                      90                     110
       TCGGCTTCTATCGCCGGGAGGGCGGTTGAGGCGGTGGTGGCGGCGTCGGCGGCGGCCGGC 130                     150                     170
       GCTGGCTGAGGGGCGCTGAGGCGGGAGCTGTGGCGCTGGGCGCCCTGGCTCCTCGGCCT 190                     210                     230
       CTGCCGGCCATGGGCTCCGAGAAGGACTCCGAGTCGCCGCGCTCCACATCGCTACATGCG
                     M   G   S   E   K   D   S   E   S   P   R   S   T   S   L   H   A       17

250                     270                     290
       GCCGCACCCGACCCTAAGTGCCGCAGCGGCGGCCGGCGCCGGCGCCTCACCTTGCACAGC
         A   A   P   D   P   K   C   R   S   G   G   R   R   R   R   L   T   L   H   S       37

310                     330                     350
       GTCTTCTCTGCCTCGGCCCGCGGCCGCCGCGCCCGGGCCAAGCCGCAGGCCGAGCCGCCG
         V   F   S   A   S   A   R   G   R   R   A   R   A   K   P   Q   A   E   P   P       57

370                     390                     410
       CCCCCGGCTGCGCCGCCGCCGCCCGCCCCGGCCCCTGCCGCGGCCCAGGGCCCCGCCGCCC
         P   P   A   A   P   P   P   P   A   P   A   P   A   A   A   Q   G   P   P   P       77

430                     450                     470
       GAGGCGCTGCCCGCCGAGCCGGCCGCCGAGGCCGAGGCGGAGGCCGCGGCGGCGGGGCG
         E   A   L   P   A   E   P   A   A   E   A   E   A   E   A   A   A   A   G   A       97

490                     510                     530
       GAGCCTGGGTTCGACGATGAGGAGGCGGCGGAGGGCGGTGGCCCGGGCGGGGAGGAGGTG
         E   P   G   F   D   D   E   E   A   A   E   G   G   P   G   G   E   E   V       117

550                     570                     590
       GAGTGTCCGCTGTGCCTGGTGCGGCTGCCGCCTGAGCGGGCCCCGCGCCTCCTCAGCTGT
         E   C   P   L   C   L   V   R   L   P   P   E   R   A   P   R   L   L   S   C       137

610                     630                     650
       CCGCACCGCTCGTGCCGGGACTGCCTCCGCCACTACCTGCGCCTGGAGATAAGCGAGAGC
         P   H   R   S   C   R   D   C   L   R   H   Y   L   R   L   E   I   S   E   S       157
```

FIGURE 1-1

```
               670                    690                   710
    AGGGTGCCCATCAGCTGCCCCGAGTGCAGCGAGCGACTCAACCCGCACGACATCCGCTTG
     R   V   P   I   S   C   P   E   C   S   E   R   L   N   P   H   D   I   R   L    177

730                    750                   770
    CTGCTCGCCGACCCGCCGCTTATGCACAAGTACGAGGAGTTCATCGTGCGCCGCTACCTA
     L   L   A   D   P   P   L   M   H   K   Y   E   E   F   I   V   R   R   Y   L    197

790                    810                   830
    GCCTCGGACCCCGACTGCCGCTGGTGCCCGGCCCCGGACTGCGGTTATGCTGTTATTGCC
     A   S   D   P   D   C   R   W   C   P   A   P   D   C   G   Y   A   V   I   A    217

850                    870                   890
    TATGGCTGTGCCAGCTGCCCGAAGCTAACTTGTGAGAGGGAAGGTTGCCAGACTGAGTTC
     Y   G   C   A   S   C   P   K   L   T   C   E   R   E   G   C   Q   T   E   F    237

910                    930                   950
    TGCTACCACTGCAAGCAGATATGGCATCCAAATCAGACATGCGATATGGCCCGTCAACAG
     C   Y   H   C   K   Q   I   W   H   P   N   Q   T   C   D   M   A   R   Q   Q    257

970                    990                  1010
    AGGGCCCAGACTTTACGAGTTCGGACCAAACACACTTCAGGTCTCAGTTATGGGCAAGAA
     R   A   Q   T   L   R   V   R   T   K   H   T   S   G   L   S   Y   G   Q   E    277

1030                   1050                  1070
    TCTGGACCAGATGACATCAAGCCATGCCCACGATGCAGTGCATACATTATCAAGATGAAT
     S   G   P   D   D   I   K   P   C   P   R   C   S   A   Y   I   I   K   M   N    297

1090                   1110                  1130
    GATGGAAGCTGTAATCACATGACCTGTGCAGTGTGTGGCTGTGAATTCTGTTGGCTTTGT
     D   G   S   C   N   H   M   T   C   A   V   C   G   C   E   F   C   W   L   C    317

1150                   1170                  1190
    ATGAAAGAGATCTCAGACTTGCATTACCTCAGCCCCTCTGGCTGTACATTCTGGGGCAAG
     M   K   E   I   S   D   L   H   Y   L   S   P   S   G   C   T   F   W   G   K    337

1210                   1230                  1250
    AAGCCATGGAGCCGTAAGAAGAAAATTCTTTGGCAGCTGGGCACGTTGATTGGTGCTCCA
     K   P   W   S   R   K   K   K   I   L   W   Q   L   G   T   L   I   G   A   P    357

1270                   1290                  1310
    GTGGGGATTTCTCTCATTGCTGGCATTGCCATTCCTGCCATGGTCATTGGCATTCCTGTT
     V   G   I   S   L   I   A   G   I   A   I   P   A   M   V   I   G   I   P   V    377
```

FIGURE 1-2

```
          1330                    1350                    1370
TATGTTGGAAGGAAGATTCACAGCAGGTATGAGGGAAGGAAAACCTCCAAACACAAGAGG
  Y   V   G   R   K   I   H   S   R   Y   E   G   R   K   T   S   K   H   K   R    397

1390                    1410                    1430
AATTTGGCTATCACTGGAGGAGTGACTTTGTCGGTCATTGCATCCCCAGTTATTGCTGCA
  N   L   A   I   T   G   G   V   T   L   S   V   I   A   S   P   V   I   A   A    417

1450                    1470                    1490
GTTAGTGTTGGTATTGGTGTCCCCATTATGCTGGCATATGTTTATGGGGTTGTGCCCATT
  V   S   V   G   I   G   V   P   I   M   L   A   Y   V   Y   G   V   V   P   I    437

1510                    1530                    1550
TCTCTTTGTCGTGGAGGTGGCTATGGAGTTAGCACAGCCAACGGAAAAGGAGTGAAAATT
  S   L   C   R   G   G   G   Y   G   V   S   T   A   N   G   K   G   V   K   I    457

1570                    1590                    1610
GAATTTGATGAAGATGATGGTCCAATCACAGTGGCAGATGCCTGGAGAGCCCTCAAGAAT
  E   F   D   E   D   D   G   P   I   T   V   A   D   A   W   R   A   L   K   N    477

1630                    1650                    1670
CCCAGCATTGGGGAAAGCAGCATTGAAGGCCTGACTAGTGTATTGAGCACTAGTGGAAGC
  P   S   I   G   E   S   S   I   E   G   L   T   S   V   L   S   T   S   G   S    497

1690                    1710                    1730
CCTACAGATGGACTTAGTGTTATGCAAGGTCCTTACAGCGAAACGGCCAGCTTTGCAGCC
  P   T   D   G   L   S   V   M   Q   G   P   Y   S   E   T   A   S   F   A   A    517

1750                    1770                    1790
CTCTCAGGGGGCACGCTGAGTGGCGGCATTCTCTCCAGTGGCAAGGGAAAATATAGCAGG
  L   S   G   G   T   L   S   G   G   I   L   S   S   G   K   G   K   Y   S   R    537

1810                    1830                    1850
TTAGAAGTTCAAGCCGATGTCCAAAAGGAAATTTTCCCCAAAGACACAGCCAGTCTTGGT
  L   E   V   Q   A   D   V   Q   K   E   I   F   P   K   D   T   A   S   L   G    557

1870                    1890                    1910
GCAATTAGTGACAACGCAAGCACTCGTGCTATGGCCGGTTCCATAATCAGTTCCTACAAC
  A   I   S   D   N   A   S   T   R   A   M   A   G   S   I   I   S   S   Y   N    577

1930                    1950                    1970
CCACAGGACAGGTTTAGCATGATCCATGCATGACTCAGCAAAGTGGATTTTGTCTCCACA
  P   Q   D   R   F   S   M   I   H   A   *
```

FIGURE 1-3

```
         1990              2010              2030
GAGAATGCAACAATATGGAAATCCAAGTGGACATTGAAGCCAAACCAAGCCACTATCAGC 2050              2070              2090
TGGTGAGTGGAAGCAGCACGGAGGACTCGCTCCATGTTCATGCTCAGATGGCAGAGAATG 2110              2130              2150
AAGAAGAAGGTAGTGGTGGCGGAGGCAGTGAAGAGGATCCCCCCTGCAGACACCAAAGCT 2170              2190              2210
GTGAACAGAAAGACTGCCTGGCCAGCAAACCTTGGGACATCAGCCTGGCCCAGCCTGAAA 2230              2250              2270
GCATCCGCAGTGACCTAGAGAGTTCTGATGCACAGTCAGACGATGTGCCAGACATCACCT 2290              2310              2330
CAGATGAGTGTGGCTCCCCCCGCTCCCATACTGCAGCCTGCCCCTCGACCCCCAGAGCCC 2350              2370              2390
AAGGTGCACCGAGCCCAAGTGCCCATATGAACCTCTCTGCCCTAGCCGAGGGACAAACTG 2410              2430              2450
TCTTGAACCCAGAAGGTGGAGAAGCCAGAGTATGAAGTGGAATGAATGCTCCTGTTCTGA 2470              2490              2510
GAAGCACACTTGTAACTGCATCTTTTGGAATTTTTTTTTTTTTTTCCAAGGGGTAGAG 2530              2550              2570
ATTTATGTATTTTATTTCACAGATTCTCTGGTCACAGGTTTTTGCCCAGGGAAATTCTGA 2590              2610              2630
GAAATTCACAATTTCTTACCAGATAAAACATGAAAAGTTTGCCGTTAGTTCCCCTCCCCT 2650              2670              2690
CCCCTCCCTCTTTTTAGTTTTAATTTATTAGTTAAACTGATGGCAGCAATCCATGAGGTG 2710              2730              2750
TGTCAAAGAGTGTACATATGTATGTGTATATTGAATGCTAGAACATATTACTGAAAGA 2770              2790              2810
CACATTTTAATAAAGATTTCTGTCATAAAAAAAAAAAAAAAAAAAAAAAAAAAAAAAAA

AAA
```

FIGURE 1-4

Amino acid composition of natural killer lytic associated protein

| | | | |
|---|---|---|---|
| 62 | Alanine | Ala | A |
| 39 | Arginine | Arg | R |
| 9 | Asparagine | Asn | N |
| 24 | Aspartic acid | Asp | D |
| 28 | Cysteine | Cys | C |
| 14 | Glutamine | Gln | Q |
| 36 | Glutamic acid | Glu | E |
| 54 | Glycine | Gly | G |
| 14 | Histidine | His | H |
| 35 | Isoleucine | Ile | I |
| 41 | Leucine | Leu | L |
| 26 | Lysine | Lys | K |
| 11 | Methionine | Met | M |
| 10 | Phenylalanine | Phe | F |
| 53 | Proline | Pro | P |
| 56 | Serine | Ser | S |
| 23 | Threonine | Thr | T |
| 7 | Tryptophan | Trp | W |
| 17 | Tyrosine | Tyr | Y |
| 28 | Valine | Val | V |

FIG 2

EXPRESSION OF NKLAM IN NK3.3 CELLS AFTER
CYTOKINE STIMULATION

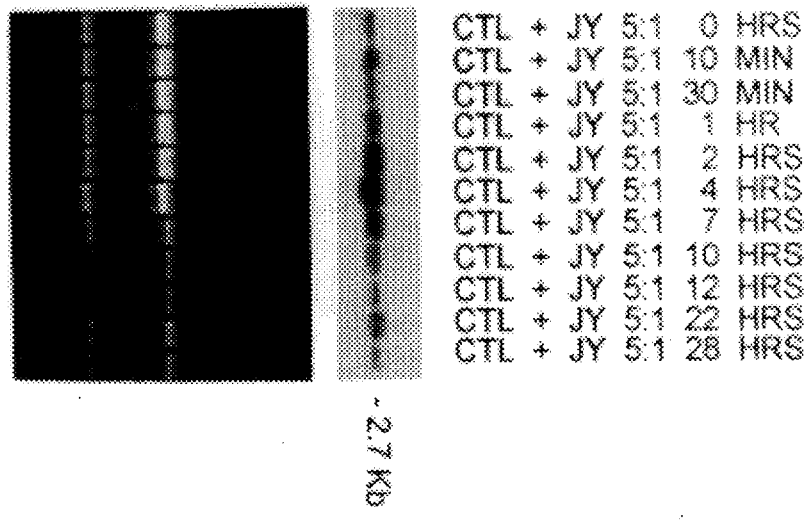
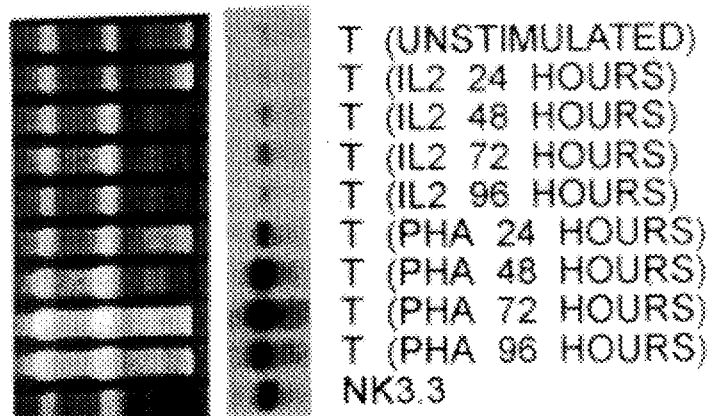
Figure 7

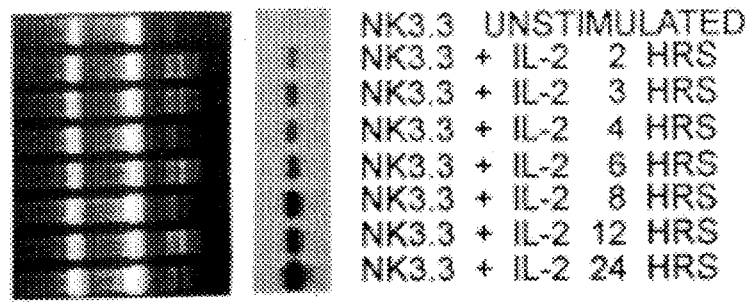
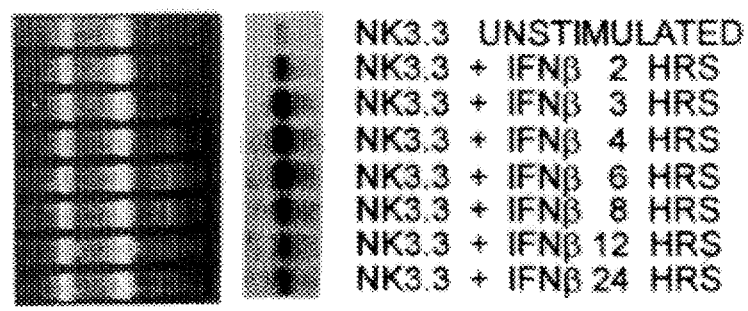
Figure 11

SEQUENCE LISTING ( 1 ) GENERAL INFORMATION:

( i i i ) NUMBER OF SEQUENCES: 17

( 2 ) INFORMATION FOR SEQ ID NO: 1:

( i ) SEQUENCE CHARACTERISTICS:
        ( A ) LENGTH: 2823 base pairs
        ( B ) TYPE: nucleic acid
        ( C ) STRANDEDNESS: double- stranded
        ( D ) TOPOLOGY: unknown ( i i ) MOLECULE TYPE: cDNA ( i i i ) HYPOTHETICAL: no ( i v ) ANTI-SENSE: no ( v ) SEQUENCE DESCRIPTION: SEQ ID NO:1:

| | | | | | | |
|---|---|---|---|---|---|---|
| CGCCTGCGCA | GGGCAGCGGC | CCGCGGGGCG | GAGGCTTTAT | AATCACTTCG | TCGTTGCCGC | 60 |
| TCGGCTTCTA | TCGCCGGGAG | GGCGGTTGAG | GCGGTGGTGG | CGGCGTCGGC | GGCGGCCGGC | 120 |
| GCTGGCTGAG | GGGCGCTGAG | GCGGGAGCTG | TGGCGCTGGG | CGCCCCTGGC | TCCTCGGCCT | 180 |
| CTGCCGGCCA | TGGGCTCCGA | GAAGGACTCC | GAGTCGCCGC | GCTCCACATC | GCTACATGCG | 240 |
| GCCGCACCCG | ACCCTAAGTG | CCGCAGCGGC | GGCCGGCGCC | GGCGCCTCAC | CTTGCACAGC | 300 |
| GTCTTCTCTG | CCTCGGCCCG | CGGCCGCCGC | GCCCGGGCCA | AGCCGCAGGC | CGAGCCGCCG | 360 |
| CCCCCGGCTG | CGCCGCCGCC | GCCCGCCCCG | GCCCTGCCG | CGGCCCAGGG | CCCGCCGCCC | 420 |
| GAGGCGCTGC | CCGCCGAGCC | GGCCGCCGAG | GCCGAGGCGG | AGGCCGCGGC | GGCGGGGGCG | 480 |
| GAGCCTGGGT | TCGACGATGA | GGAGGCGGCG | GAGGGCGGTG | GCCCGGGCGG | GGAGGAGGTG | 540 |
| GAGTGTCCGC | TGTGCCTGGT | GCGGCTGCCG | CCTGAGCGGG | CCCCGCGCCT | CCTCAGCTGT | 600 |
| CCGCACCGCT | CGTGCCGGGA | CTGCCTCCGC | CACTACCTGC | GCCTGGAGAT | AAGCGAGAGC | 660 |
| AGGGTGCCCA | TCAGCTGCCC | CGAGTGCAGC | GAGCGACTCA | ACCGCACGA | CATCCGCTTG | 720 |
| CTGCTCGCCG | ACCCGCCGCT | TATGCACAAG | TACGAGGAGT | TCATCGTGCG | CCGCTACCTA | 780 |
| GCCTCGGACC | CCGACTGCCG | CTGGTGCCCG | GCCCCGGACT | GCGGTTATGC | TGTTATTGCC | 840 |
| TATGGCTGTG | CCAGCTGCCC | GAAGCTAACT | TGTGAGAGGG | AAGGTTGCCA | GACTGAGTTC | 900 |
| TGCTACCACT | GCAAGCAGAT | ATGGCATCCA | AATCAGACAT | GCGATATGGC | CCGTCAACAG | 960 |
| AGGGCCCAGA | CTTTACGAGT | TCGGACCAAA | CACACTTCAG | GTCTCAGTTA | TGGGCAAGAA | 1020 |
| TCTGGACCAG | ATGACATCAA | GCCATGCCCA | CGATGCAGTG | CATACATTAT | CAAGATGAAT | 1080 |
| GATGGAAGCT | GTAATCACAT | GACCTGTGCA | GTGTGTGGCT | GTGAATTCTG | TTGGCTTTGT | 1140 |
| ATGAAAGAGA | TCTCAGACTT | GCATTACCTC | AGCCCCTCTG | GCTGTACATT | CTGGGGCAAG | 1200 |
| AAGCCATGGA | GCCGTAAGAA | GAAAATTCTT | TGGCAGCTGG | GCACGTTGAT | TGGTGCTCCA | 1260 |
| GTGGGGATTT | CTCTCATTGC | TGGCATTGCC | ATTCCTGCCA | TGGTCATTGG | CATTCCTGTT | 1320 |
| TATGTTGGAA | GGAAGATTCA | CAGCAGGTAT | GAGGGAAGGA | AAACCTCCAA | ACACAAGAGG | 1380 |
| AATTTGGCTA | TCACTGGAGG | AGTGACTTTG | TCGGTCATTG | CATCCCAGT | TATTGCTGCA | 1440 |
| GTTAGTGTTG | GTATTGGTGT | CCCCATTATG | CTGGCATATG | TTTATGGGGT | TGTGCCCATT | 1500 |
| TCTCTTTGTC | GTGGAGGTGG | CTATGGAGTT | AGCACAGCCA | ACGGAAAAGG | AGTGAAAATT | 1560 |
| GAATTTGATG | AAGATGATGG | TCCAATCACA | GTGGCAGATG | CCTGGAGAGC | CCTCAAGAAT | 1620 |
| CCCAGCATTG | GGGAAAGCAG | CATTGAAGGC | CTGACTAGTG | TATTGAGCAC | TAGTGGAAGC | 1680 |

-continued

```
CCTACAGATG GACTTAGTGT TATGCAAGGT CCTTACAGCG AAACGGCCAG CTTTGCAGCC    1740
CTCTCAGGGG GCACGCTGAG TGGCGGCATT CTCTCCAGTG GCAAGGGAAA ATATAGCAGG    1800
TTAGAAGTTC AAGCCGATGT CCAAAAGGAA ATTTTCCCCA AAGACACAGC CAGTCTTGGT    1860
GCAATTAGTG ACAACGCAAG CACTCGTGCT ATGGCCGGTT CCATAATCAG TTCCTACAAC    1920
CCACAGGACA GGTTTAGCAT GATCCATGCA TGACTCAGCA AAGTGGATTT TGTCTCCACA    1980
GAGAATGCAA CAATATGGAA ATCCAAGTGG ACATTGAAGC CAAACCAAGC CACTATCAGC    2040
TGGTGAGTGG AAGCAGCACG GAGGACTCGC TCCATGTTCA TGCTCAGATG GCAGAGAATG    2100
AAGAAGAAGG TAGTGGTGGC GGAGGCAGTG AAGAGGATCC CCCTGCAGA CACCAAAGCT     2160
GTGAACAGAA AGACTGCCTG GCCAGCAAAC CTTGGGACAT CAGCCTGGCC CAGCCTGAAA    2220
GCATCCGCAG TGACCTAGAG AGTTCTGATG CACAGTCAGA CGATGTGCCA GACATCACCT    2280
CAGATGAGTG TGGCTCCCCC CGCTCCCATA CTGCAGCCTG CCCCTCGACC CCCAGAGCCC    2340
AAGGTGCACC GAGCCCAAGT GCCCATATGA ACCTCTCTGC CTAGCCGAG GGACAAACTG     2400
TCTTGAACCC AGAAGGTGGA GAAGCCAGAG TATGAAGTGG AATGAATGCT CCTGTTCTGA    2460
GAAGCACACT TGTAACTGCA TCTTTTGGAA TTTTTTTTTT TTTTTTCCA AGGGGTAGAG     2520
ATTTATGTAT TTTATTTCAC AGATTCTCTG GTCACAGGTT TTTGCCCAGG GAAATTCTGA    2580
GAAATTCACA ATTTCTTACC AGATAAAACA TGAAAAGTTT GCCGTTAGTT CCCCTCCCCT    2640
CCCCTCCCTC TTTTTAGTTT TAATTTATTA GTTAAACTGA TGGCAGCAAT CCATGAGGTG    2700
TGTCAAAGAG TGTACATATG TATGTGTGTA TATTGAATGC TAGAACATAT TACTGAAAGA    2760
CACATTTTAA TAAAGATTTC TGTCATAAAA AAAAAAAAA AAAAAAAAAA AAAAAAAAA     2820
AAA                                                                 2823
```

(2) INFORMATION FOR SEQ ID NO: 2:

(i) SEQUENCE CHARACTERISTICS:
    (A) LENGTH: 587
    (B) TYPE: amino acid
    (C) STRANDEDNESS:
    (D) TOPOLOGY: linear (ii) MOLECULE TYPE: Protein (iii) HYPOTHETICAL: No (iv) ANTI-SENSE: No (v) SEQUENCE DESCRIPTION: SEQ ID NO:2:

```
Met Gly Ser Glu Lys Asp Ser Glu Ser Pro Arg Ser Thr Ser Leu His Ala
                5                  10                  15
Ala Ala Pro Asp Pro Lys Cys Arg Ser Gly Gly Arg Arg Arg Arg Leu Thr
            20                  25                  30
Leu His Ser Val Phe Ser Ala Ser Ala Arg Gly Arg Arg Ala Arg Ala Lys
 35                  40                  45                  50
Pro Gln Ala Glu Pro Pro Pro Ala Ala Pro Pro Pro Ala Pro Ala
                55                  60                  65
Pro Ala Ala Ala Gln Gly Pro Pro Glu Ala Leu Pro Ala Glu Pro Ala
 70                  75                  80                  85
Ala Glu Ala Glu Ala Glu Ala Ala Ala Ala Gly Ala Glu Pro Gly Phe Asp
                90                  95                 100
Asp Glu Glu Ala Ala Glu Gly Gly Gly Pro Gly Gly Glu Glu Val Glu Cys
            105                 110                 115
Pro Leu Cys Leu Val Arg Leu Pro Pro Glu Arg Ala Pro Arg Leu Leu Ser
120                 125                 130                 135
```

-continued

```
Cys Pro His Arg Ser Cys Arg Asp Cys Leu Arg His Tyr Leu Arg Leu Glu
        140                 145                 150
Ile Ser Glu Ser Arg Val Pro Ile Ser Cys Pro Glu Cys Ser Glu Arg Leu
    155                 160                 165                 170
Asn Pro His Asp Ile Arg Leu Leu Leu Ala Asp Pro Pro Leu Met His Lys
                175                 180                 185
Tyr Glu Glu Phe Ile Val Arg Arg Tyr Leu Ala Ser Asp Pro Asp Cys Arg
        190                 195                 200
Trp Cys Pro Ala Pro Asp Cys Gly Tyr Ala Val Ile Ala Tyr Gly Cys Ala
205             210                 215                 220
Ser Cys Pro Lys Leu Thr Cys Glu Arg Glu Gly Cys Gln Thr Glu Phe Cys
            225                 230                 235
Tyr His Cys Lys Gln Ile Trp His Pro Asn Gln Thr Cys Asp Met Ala Arg
    240                 245                 250                 255
Gln Gln Arg Ala Gln Thr Leu Arg Val Arg Thr Lys His Thr Ser Gly Leu
                260                 265                 270
Ser Tyr Gly Gln Glu Ser Gly Pro Asp Asp Ile Lys Pro Cys Pro Arg Cys
        275                 280                 285
Ser Ala Tyr Ile Ile Lys Met Asn Asp Gly Ser Cys Asn His Met Thr Cys
290                 295                 300                 305
Ala Val Cys Gly Cys Glu Phe Cys Trp Leu Cys Met Lys Glu Ile Ser Asp
            310                 315                 320
Leu His Tyr Leu Ser Pro Ser Gly Cys Thr Phe Trp Gly Lys Lys Pro Trp
    325                 330                 335                 340
Ser Arg Lys Lys Lys Ile Leu Trp Gln Leu Gly Thr Leu Ile Gly Ala Pro
                345                 350                 355
Val Gly Ile Ser Leu Ile Ala Gly Ile Ala Ile Pro Ala Met Val Ile Gly
        360                 365                 370
Ile Pro Val Tyr Val Gly Arg Lys Ile His Ser Arg Tyr Glu Gly Arg Lys
375                 380                 385                 390
Thr Ser Lys His Lys Arg Asn Leu Ala Ile Thr Gly Gly Val Thr Leu Ser
            395                 400                 405
Val Ile Ala Ser Pro Val Ile Ala Ala Val Ser Val Gly Ile Gly Val Pro
    410                 415                 420                 425
Ile Met Leu Ala Tyr Val Tyr Gly Val Val Pro Ile Ser Leu Cys Arg Gly
                430                 435                 440
Gly Gly Tyr Gly Val Ser Thr Ala Asn Gly Lys Gly Val Lys Ile Glu Phe
        445                 450                 455
Asp Glu Asp Asp Gly Pro Ile Thr Val Ala Asp Ala Trp Arg Ala Leu Lys
460                 465                 470                 475
Asn Pro Ser Ile Gly Glu Ser Ser Ile Glu Gly Leu Thr Ser Val Leu Ser
            480                 485                 490
Thr Ser Gly Ser Pro Thr Asp Gly Leu Ser Val Met Gln Gly Pro Tyr Ser
    495                 500                 505                 510
Glu Thr Ala Ser Phe Ala Ala Leu Ser Gly Gly Thr Leu Ser Gly Gly Ile
                515                 520                 525
Leu Ser Ser Gly Lys Gly Lys Tyr Ser Arg Leu Glu Val Gln Ala Asp Val
        530                 535                 540
Gln Lys Glu Ile Phe Pro Lys Asp Thr Ala Ser Leu Gly Ala Ile Ser Asp
545                 550                 555                 560
Asn Ala Ser Thr Arg Ala Met Ala Gly Ser Ile Ile Ser Ser Tyr Asn Pro
            565                 570                 575
Gln Asp Arg Phe Ser Met Ile His Ala
```

( 2 ) INFORMATION FOR SEQ ID NO: 3:

( i ) SEQUENCE CHARACTERISTICS:
        ( A ) LENGTH: 17 base pairs
        ( B ) TYPE: nucleic acid
        ( C ) STRANDEDNESS: double-stranded
        ( D ) TOPOLOGY: linear ( i i ) MOLECULE TYPE: DNA ( i i i ) HYPOTHETICAL: no ( i v ) ANTI-SENSE: Yes ( v ) SEQUENCE DESCRIPTION: SEQ ID NO:3:

AAGTCTGGGC CCTCTGT        17

( 2 ) INFORMATION FOR SEQ ID NO: 4:

( i ) SEQUENCE CHARACTERISTICS:
        ( A ) LENGTH: 17 base pairs
        ( B ) TYPE: nucleic acid
        ( C ) STRANDEDNESS: double-stranded
        ( D ) TOPOLOGY: linear ( i i ) MOLECULE TYPE: DNA ( i i i ) HYPOTHETICAL: no ( i v ) ANTI-SENSE: Yes ( v ) SEQUENCE DESCRIPTION: SEQ ID NO:4:

ACAGAGGGCC CAGACTT        17

( 2 ) INFORMATION FOR SEQ ID NO: 5:

( i ) SEQUENCE CHARACTERISTICS:
        ( A ) LENGTH: 17 base pairs
        ( B ) TYPE: nucleic acid
        ( C ) STRANDEDNESS: double-stranded
        ( D ) TOPOLOGY: linear ( i i ) MOLECULE TYPE: DNA ( i i i ) HYPOTHETICAL: no ( i v ) ANTI-SENSE: no ( v ) SEQUENCE DESCRIPTION: SEQ ID NO:5:

TGGAAGCTGT AATCACA        17

( 2 ) INFORMATION FOR SEQ ID NO: 6:

( i ) SEQUENCE CHARACTERISTICS:
        ( A ) LENGTH: 17 base pairs
        ( B ) TYPE: nucleic acid
        ( C ) STRANDEDNESS: double-stranded
        ( D ) TOPOLOGY: linear ( i i ) MOLECULE TYPE: DNA ( i i i ) HYPOTHETICAL: no ( i v ) ANTI-SENSE: no ( v ) SEQUENCE DESCRIPTION: SEQ ID NO:6:

TCTCATTGCT GGCATTG        17

( 2 ) INFORMATION FOR SEQ ID NO: 7:

( i ) SEQUENCE CHARACTERISTICS:
    ( A ) LENGTH: 17 base pairs
    ( B ) TYPE: nucleic acid
    ( C ) STRANDEDNESS: double-stranded
    ( D ) TOPOLOGY: linear ( i i ) MOLECULE TYPE: DNA ( i i i ) HYPOTHETICAL: no ( i v ) ANTI-SENSE: no ( v ) SEQUENCE DESCRIPTION: SEQ ID NO:7:

```
          GTGGAGGTGG CTATGGA                                   17
```

( 2 ) INFORMATION FOR SEQ ID NO: 8:

( i ) SEQUENCE CHARACTERISTICS:
    ( A ) LENGTH: 17 base pairs
    ( B ) TYPE: nucleic acid
    ( C ) STRANDEDNESS: double-stranded
    ( D ) TOPOLOGY: linear ( i i ) MOLECULE TYPE: DNA ( i i i ) HYPOTHETICAL: no ( i v ) ANTI-SENSE: no ( v ) SEQUENCE DESCRIPTION: SEQ ID NO:8:

```
          TGAGTGGCGG CATTCTC                                   17
```

( 2 ) INFORMATION FOR SEQ ID NO: 9:

( i ) SEQUENCE CHARACTERISTICS:
    ( A ) LENGTH: 17 base pairs
    ( B ) TYPE: nucleic acid
    ( C ) STRANDEDNESS: double-stranded
    ( D ) TOPOLOGY: linear ( i i ) MOLECULE TYPE: DNA ( i i i ) HYPOTHETICAL: no ( i v ) ANTI-SENSE: no ( v ) SEQUENCE DESCRIPTION: SEQ ID NO:9:

```
          CAAGACAGTT TGTCCTC                                   17
```

( 2 ) INFORMATION FOR SEQ ID NO: 10:

( i ) SEQUENCE CHARACTERISTICS:
    ( A ) LENGTH: 17 base pairs
    ( B ) TYPE: nucleic acid
    ( C ) STRANDEDNESS: double-stranded
    ( D ) TOPOLOGY: linear ( i i ) MOLECULE TYPE: DNA ( i i i ) HYPOTHETICAL: no ( i v ) ANTI-SENSE: no ( v ) SEQUENCE DESCRIPTION: SEQ ID NO:10:

```
          GGTTCATATG GGCACTT                                   17
```

( 2 ) INFORMATION FOR SEQ ID NO: 11:

( i ) SEQUENCE CHARACTERISTICS:
    ( A ) LENGTH: 17 base pairs
    ( B ) TYPE: nucleic acid ( C ) STRANDEDNESS: double-stranded
( D ) TOPOLOGY: linear ( i i ) MOLECULE TYPE: DNA ( i i i ) HYPOTHETICAL: no ( i v ) ANTI-SENSE: no ( v ) SEQUENCE DESCRIPTION: SEQ ID NO:11:

GGCAGCTGAT GGGCACC 17

( 2 ) INFORMATION FOR SEQ ID NO: 12:

( i ) SEQUENCE CHARACTERISTICS:
( A ) LENGTH: 18 base pairs
( B ) TYPE: nucleic acid
( C ) STRANDEDNESS: double-stranded
( D ) TOPOLOGY: linear ( i i ) MOLECULE TYPE: DNA ( i i i ) HYPOTHETICAL: no ( i v ) ANTI-SENSE: no ( v ) SEQUENCE DESCRIPTION: SEQ ID NO:12:

GGACCCCGAC TGCCGCTG 18

( 2 ) INFORMATION FOR SEQ ID NO: 13:

( i ) SEQUENCE CHARACTERISTICS:
( A ) LENGTH: 18 base pairs
( B ) TYPE: nucleic acid
( C ) STRANDEDNESS: double-stranded
( D ) TOPOLOGY: linear ( i i ) MOLECULE TYPE: DNA ( i i i ) HYPOTHETICAL: no ( i v ) ANTI-SENSE: no ( v ) SEQUENCE DESCRIPTION: SEQ ID NO:13:

CAGCGGCAGT CGGGGTCC 18

( 2 ) INFORMATION FOR SEQ ID NO: 14:

( i ) SEQUENCE CHARACTERISTICS:
( A ) LENGTH: 18 base pairs
( B ) TYPE: nucleic acid
( C ) STRANDEDNESS: double-stranded
( D ) TOPOLOGY: linear ( i i ) MOLECULE TYPE: DNA ( i i i ) HYPOTHETICAL: no ( i v ) ANTI-SENSE: no ( v ) SEQUENCE DESCRIPTION: SEQ ID NO:14:

TCCACATCGC TACATGCG 18

( 2 ) INFORMATION FOR SEQ ID NO: 15:

( i ) SEQUENCE CHARACTERISTICS:
( A ) LENGTH: 17 base pairs
( B ) TYPE: nucleic acid
( C ) STRANDEDNESS: double-stranded
( D ) TOPOLOGY: linear ( i i ) MOLECULE TYPE: DNA -continued (iii) HYPOTHETICAL: no (iv) ANTI-SENSE: no (v) SEQUENCE DESCRIPTION: SEQ ID NO:15:

ACAGAGGGCC CAGACTT    17

(2) INFORMATION FOR SEQ ID NO: 16:

(i) SEQUENCE CHARACTERISTICS:
(A) LENGTH: 17 base pairs
(B) TYPE: nucleic acid
(C) STRANDEDNESS: double-stranded
(D) TOPOLOGY: linear (ii) MOLECULE TYPE: DNA (iii) HYPOTHETICAL: no (iv) ANTI-SENSE: no (v) SEQUENCE DESCRIPTION: SEQ ID NO:16:

GACAACGCAA GCACTCG    17

(2) INFORMATION FOR SEQ ID NO: 17:

(i) SEQUENCE CHARACTERISTICS:
(A) LENGTH: 19 base pairs
(B) TYPE: nucleic acid
(C) STRANDEDNESS: double-stranded
(D) TOPOLOGY: linear (ii) MOLECULE TYPE: DNA (iii) HYPOTHETICAL: no (iv) ANTI-SENSE: no (v) SEQUENCE DESCRIPTION: SEQ ID NO:17:

ATGCCTTCTC GGAGCCCAT    19

DNA ENCODING NATURAL KILLER LYTIC ASSOCIATED PROTEIN

CROSS-REFERENCE TO RELATED APPLICATION

This application is a continuation-in-part of application Ser. No. 08/126,501, filed Sep. 24, 1993, now abandoned.

FEDERAL FUNDING NOTICE

This invention was made utilizing funds of the United States government. The U.S. government is therfore granted a royalty-free, nonexclusive, world-wide, paid-up license in this invention.

BACKGROUND OF THE INVENTION

1. Field of the Invention

The present invention relates generally to the fields of molecular biology and immunology. More specifically, the present invention relates to DNA encoding the natural killer lytic associated protein ("NKLAP") and uses thereof.

2. Description of Related Art

Natural killer (NK) cells are large granular lymphocytes which lyse tumor and virus-infected cells without prior sensitization. Natural killer cells play a role in natural resistance against both solid tumors and hematopoietic tumors. M. Introna & A. Montovani, "Natural Killer Cells in Human Solid Tumors," *Cancer Metastasis Rev.*, 2:337 (1983). In addition, natural killer cells have antimicrobial activity, giving them a role in combating diseases caused by bacteria, fungi, yeast, and protozoal parasites.

Although resident natural killer cells have the ability to kill select target cells in normal individuals, they are not able to kill most primary tumors. Natural killer activity decreases as a function of age, which may contribute to the incidence of tumors with age. It has also been found that natural killer cells from cancer patients are often incapable of killing tumor cells. Thus, a better understanding of the molecular and cellular events involved with natural killer lytic activity would facilitate medical treatment of many diseases.

While the receptor(s) involved in the recognition of target cells by natural killer cells are as yet undefined, it is well established that natural killer activity can be augmented by several agents, including certain viruses, cytokines such as the interferons ("IFNs"), and interleukins (IL-2, IL-12). J. Kornbluth, et al., "RG: Changes in Gene Expression Associated with interferon-β and IL-2-Induced Augmentation of Human Natural Killer Cell Function," *J. Immunol.*, 141:3234–3240 (1988). In fact, IL-2 and the interferons increase natural killer lytic activity 20 to 30 fold. These cytokines activate natural killer cells to kill with greater efficiency and a broader specificity. IL-2 activated natural killer cells are responsible for the majority of the lymphokine activated killing ("LAK") activity observed in vivo. J. H. Phillips, et al., "Dissection of the Lymphokine-Activated Killer Phenomenon: Relative Contribution of Peripheral Blood Natural Killer Cells and T Lymphocytes to Cytolysis," *J. Exp. Med.*, 164:814–825 (1986). The killing activity of isolated natural killer cells from cancer patients may even be restored by culture with IL-2. A. Belldegrun, et al., "Interleukin-2 Expanded Tumor-Infiltrating Lymphocytes in Human Renal Cell Cancer: Isolation, Characterization and Antitumor Activity," *Cancer Res.* 48:206 (1988). However, a number of toxic effects associated with administration of high doses of IL-2 have been observed in treated cancer patients. M. Rosenstein, et al., "Extravasation of Intravascular Fluid Mediated by the Systemic Administration of Recombinant Interleukin-2," *J. Immunol.*, 137:1735–1742 (1986). The augmentation of natural killer lyric activity by IL-2 and interferon is independent of DNA synthesis, but requires de novo RNA and protein synthesis. J. R. Ortaldo, et al., "Effects of Metabolic Inhibitors on Spontaneous and Interferon-Boosted Human Natural Killer Cell Activity," *J. Immunol.*, 125:1839–1844 (1980). However, the molecules and mechanism involved in this enhancement have been unknown. Some researchers have theorized that one responsible mechanism is up-regulation of the adhesion molecules CD2, CD11a, and CD54. M. J. Robertson, et al., "Human Natural Killer Cell Adhesion Molecules: Differential Expression after Activation and Participation in Cytolysis," *J. Immunol.*, 145:3194–3201 (1990).

Although many recent studies have begun to focus on early membrane signal transduction events associated with the binding of IL-2 and interferon to natural killer cells, it is still unknown how these events translate into increased tumor cell recognition and lysis. Molecular and biochemical studies have previously been hampered by natural killer heterogeneity and its low concentration in the blood. One mechanism by which natural killer cells are thought to kill tumor cells is through cell to cell contact wherein a $Ca^{++}$-dependent release of perforin from cytoplasmic granules occurs. J. D. Young, "Killing of Target Cells by Lymphocyte: A Mechanistic View," *Physiological Rev.*, 69:250 (1989); P. A. Henkart, "Mechanism of Lymphocyte-Mediated Cytotoxicity," *Ann. Rev, Immunol.*, 3:31 (1985).

According to this granule exocytosis model, the stages of cytolysis are: (1) recognition and adhesion resulting in the formation of effector-target cell conjugates; (2) reorientation of the microtubule organizing center and Golgi apparatus within the effector cell; (3) movement of granules towards the site of conjugation; (4) fusion of the granules to the cell membrane with subsequent release of granule contents into the intracellular space; and (5) target cell death, resulting from the formation of membrane lesions by the $Ca^{++}$ dependent polymerization of perforin within the target cell membrane. Other mediators associated with natural killer lysis include serine esterase, natural killer cytotoxic factor, tumor necrosis factor (TNF) and TNF-like compounds. These molecules function in target cell lysis through mechanisms different from that of perforin, in some cases, inducing programmed cell death (apoptosis) in the target cells. The regulation of these events is largely unknown.

Previous attempts to identify and control the molecular and cellular events controlling natural killer and cytotoxic T lymphocyte lytic activity have been primarily unsuccessful. Consequently, an identification of the genes and their protein products associated with natural killer function is desirable. The prior art is deficient in the lack of effective means of treating neoplastic and auto-immune diseases. The present invention fulfills this longstanding need and desire in the art.

SUMMARY OF THE INVENTION

In one embodiment of the present invention, there is provided DNA encoding a natural killer lytic associated protein selected from the group consisting of: (a) isolated DNA which encodes a human natural killer lytic associated protein; (b) isolated DNA which hybridizes to isolated DNA of (a) above and which encodes a human natural killer lytic associated protein; and (c) isolated DNA differing from the isolated DNAs of (a) and (b) above in codon sequence due to the degeneracy of the genetic code, and which encodes a human natural killer lytic associated protein.

In another embodiment of the present invention, there is provided a pharmaceutical composition, comprising human natural killer lytic associated protein and a pharmaceutically acceptable carrier.

In yet another embodiment of the present invention, there is provided a plasmid adapted for expression in a recombinant cell containing the DNA of the present invention and regulatory elements necessary for expression of the DNA in the cell.

In still yet another embodiment of the present invention, there is provided a host cell transfected with the vector of the present invention, said vector expressing a natural killer lytic associated protein.

In another embodiment of the present invention, there is provided Isolated and purified natural killer lyric associated protein coded for by DNA selected from the group consisting of: (a) isolated DNA which encodes a human natural killer lytic associated protein; (b) isolated DNA which hybridizes to isolated DNA of (a) above and which encodes a human natural killer lytic associated protein; and (c) isolated DNA differing from the isolated DNAs of (a) and (b) above in codon sequence due to the degeneracy of the genetic code, and which encodes a human natural killer lyric associated protein.

In yet another embodiment of the present invention, there is provided a method of inhibiting expression of the DNA of claim 1, comprising the step of exposing said DNA to antisense oligonucleotides specific to said DNA sequence.

In still yet another embodiment of the present invention, there is provided a method of enhancing expression of the DNA of claim 1, comprising the step of exposing said DNA sequence to a cytokine.

In yet another embodiment of the present invention, there is provided a method for treating a pathophysiological state in an individual, comprising the step of administering to said individual a composition comprising a therapeutically effective dose of the plasmid of claim 4.

In yet another embodiment of the present invention, there is provided a method for treating a pathophysiological state in an individual, comprising the step of administering to said individual a composition comprising a therapeutically effective dose of an antisense oligonucleotide directed against the DNA of claim 1.

Other and further aspects, features, and advantages of the present invention will be apparent from the following description of the presently preferred embodiments of the invention given for the purpose of disclosure.

The present invention is directed to a unique DNA sequence encoding natural killer lytic associated protein. The present invention further comprises a recombinant expression vector containing a DNA sequence encoding natural killer lyric associated protein, where the vector is capable of expressing natural killer lytic associated protein in a transformed microorganism or cell culture. Accordingly, the present invention is also directed to a microorganism transformed with a vector capable of expressing natural killer lytic associated protein and to a cell culture capable of expressing natural killer lytic associated protein. Such a cell culture is obtained by transforming a mammalian cell line with a vector capable of expressing natural killerlyric associated protein.

As mentioned above, the present invention further comprises essentially pure natural killer lytic associated protein. The gene product may be produced through recombinant DNA technology in commercial quantities for use in research and human medical treatment for a wide variety of diseases. Natural killer lytic associated protein produced via this technology will be free of the contaminants normally associated with it in its non-recombinant cellular environment.

Another aspect of the invention is a method for preparing the DNA sequence encoding natural killer lyric associated protein. This method comprises the steps of preparing an interferon-$\beta$ stimulated natural killer 3.3 cDNA library; selecting cDNA from the library that are expressed at elevated levels in interferon-$\beta$ stimulated natural killer 3.3 cells; identifying the sequences of said cDNA; and isolating the cDNA sequence encoding natural killer lytic associated protein.

The invention also includes a method for preparing natural killer lytic associated protein comprising the steps of adding recombinant expression vectors containing a DNA sequence encoding natural killer lyric associated protein to a culture of microorganisms or cells; allowing the recombinant expression vectors to encode natural killer lyric associated protein; and collecting the natural killer lytic associated protein. Furthermore, methods of inhibiting and enhancing cDNA expression of natural killer lytic associated protein are part of the present invention. A method of inhibiting expression of a DNA sequence encoding natural killer lytic associated protein involves exposing the DNA sequence to antisense oligonucleotides specific to said DNA sequence. Inhibition of the expression of the natural killer lytic associated protein may be used to turn off immune responses in situations of graft rejection and autoimmune disorders. A method of enhancing expression of a DNA sequence encoding natural killer lytic associated protein involves exposing the DNA sequence to a cytokine or other suitable agent.

The present invention is also directed to a method for treating a pathophysiological state in an individual, comprising the step of administering to said individual a composition comprising a therapeutically effective dose of the plasmid of claim 4.

Still other objects, features and advantages of the present invention will be apparent from the following description of the preferred embodiments, given for the purpose of disclosure, and taken in conjunction with the accompanying drawings.

BRIEF DESCRIPTION OF THE DRAWINGS

So that the matter in which the above-recited features, advantages and object is of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the nucleotide sequence and deduced amino acid sequence of the full length natural killer lyric associated protein cDNA.

FIG. 2 shows a table showing the amino acid composition of the natural killer lytic associated protein.

FIG. 7 shows expression of natural killer lytic associated protein in CTL and PHA-activated T cells but not resting, peripheral blood T cells.

FIG. 11 shows the kinetics of natural killer lytic associated protein expression in interferon-β and IL-2 stimulated natural killer 3.3 cells.

DETAILED DESCRIPTION OF THE INVENTION

Definitions

Figure 3A:
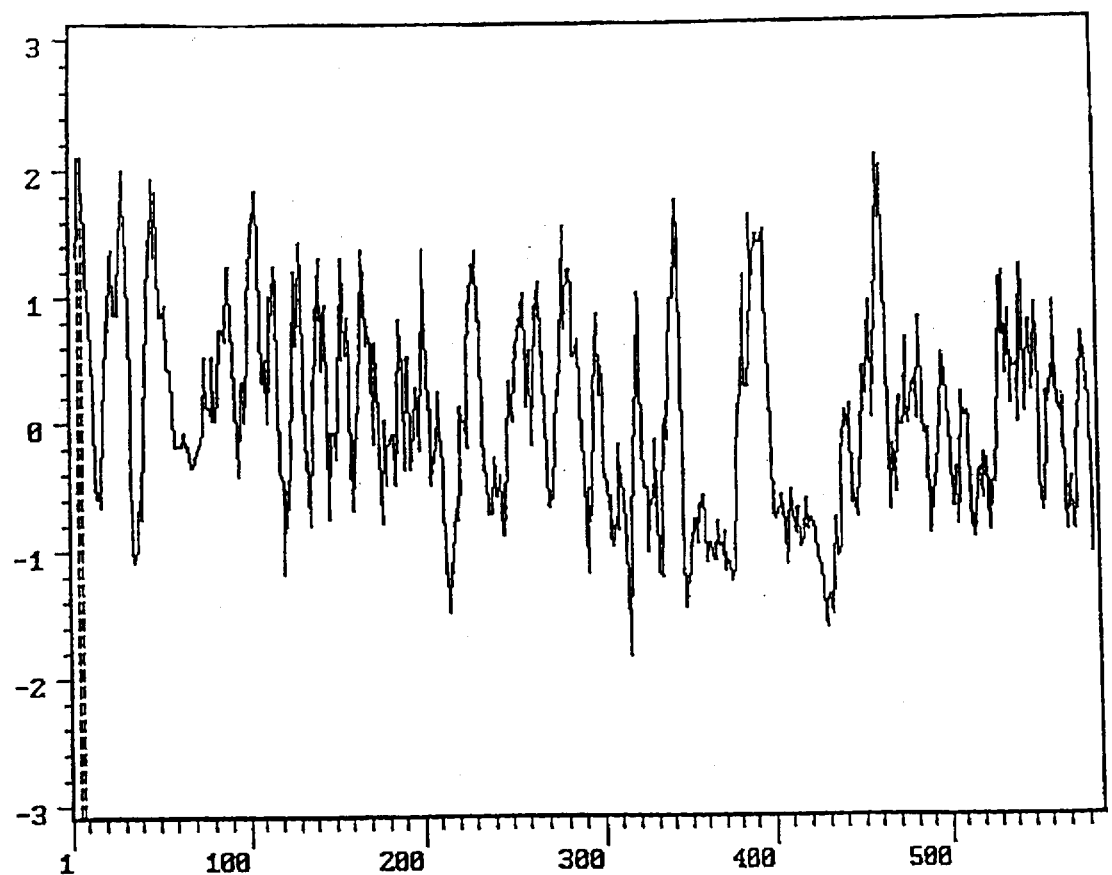
FIG. 3A shows a trace showing the hydrophilicity (and antigenicitiy) of the natural killer lytic associated protein.

The term "functional expression of the gene" is meant to include the suppression of transcription of the gene, the degradation of the gene transcript (pre-message RNA), the inhibition of splicing, the destruction of the message RNA, the prevention of translation of the message RNA, the prevention of the post-translational modifications of the protein, the destruction of the protein, or the inhibition of the normal function of the protein.

The term "transfected plasmid" is meant to include the bacterial plasmid which contains natural killer lytic associated gene to be carried (transfected) into the cell of choice.

The term "gene therapy" is meant to include the insertion of part or all of a gene, a DNA construct, RNA, or gene product into a cell, group of cells, tissue, pathologic lesion, organ or organism for the purpose of modulating gene expression, and/or function of the gene product.

The term "prophylactic gene therapy" is meant to include genes which may be used for partial or total inhibition or prevention of disease and the spread of disease and also is meant to include genes which may be used to supplement or replace absent or defective negative growth in cell, tissues or germlines.

The term "cell proliferative disease" is meant to include any human or animal disease or disorder, affecting any one or any combination of organs, cavities or body parts, which is characterized by single or multiple local abnormal proliferations of cells, groups of cells or tissue(s), whether benign or malignant.

The term "prokaryote" is meant to include all bacteria which can be transformed with the DNA for the expression of the recombinant molecules of the present invention.

The term "eukaryote" is meant to include all yeasts, fungi, animal and plant cells which can be transformed with the DNA for the expression of the recombinant molecules of the present invention.

The DNA for DNA constructs of the present invention can be synthetic or may be derived from any mammalian species. All that is required is that the genetic sequence for the natural killer lytic associated gene be functionally expressed in the prokaryotic or eukaryotic organism. Preferred is synthetic DNA.

A recombinant DNA molecule coding for the DNA constructs of the present invention can be used to transform a host using any of the techniques commonly known to those of ordinary skill in the art.

Methods for preparing fused, operably linked genes and expressing them in bacteria are known and are shown, for example, in U.S. Pat. No. 4,366,246, herein incorporated by reference. The genetic constructs and methods described therein can be utilized for construction of the DNA constructs of the present invention and transfection in prokaryotic or eukaryotic hosts.

Prokaryotic hosts may include Gram negative as well as Gram positive bacteria, such as *E. coli*, *S. tymphimurium*, *Serratia marcescens* and *Bacillus subtilis*. Eukaryotic hosts may include yeasts such as *Pichia pastoris* or mammalian cells.

In general, expression vectors containing promoter sequences which facilitate the efficient transcription of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

Examples of promoters which can be used in the invention include, but are not limited to: cytomegalovirus (CMV) promotor, human β-actin promotor, metallothionin promotor, SV40 origin of replication, MMTV LTR promotor and MuLV LTR promotor. Examples of some of the plasmids or bacteriophage which can be used in the invention are listed in Maniatis et al., *Molecular Cloning*, Cold Spring Harbor Laboratories, 1982, and others are known to those of skill in the art and can be easily ascertained.

A gene is a DNA sequence which encodes through its template or messenger RNA a sequence of amino acids characteristic of a specific peptide. The term cDNA includes genes from which the intervening sequences have been removed. The term "recombinant DNA" (rDNA) is meant to include a molecule that has been recombined by splicing cDNA or genomic DNA sequences in vitro.

A cloning vehicle is a plasmid or phage DNA or other DNA sequence which is able to replicate in a host cell which is characterized by one or a small number of endonuclease recognition sites at which such DNA sequences may be cut in a determinable fashion without loss of an essential biological function of the DNA, and which contains a marker suitable for use in the identification of transformed cells. Markers, for example, are tetracycline resistance or ampicillin resistance. The word "vector" is sometimes used for a cloning vehicle.

An expression vehicle is a vehicle similar to a cloning vehicle but which is capable of expressing a given structural gene in a host, normally under control of certain control sequences.

The term "individual" is meant to include animals and humans.

The term "biologically inhibiting" or "inhibition" of the growth of proliferating cells is meant to include partial or total growth inhibition and also is meant to include decreases in the rate of proliferation or growth of the cells. The biologically inhibitory dose of the mutants of the present invention may be determined by assessing the effects of the test element on target malignant or abnormally proliferating cell growth in tissue culture, tumor growth in animals and cell culture or any other method known to those of ordinary skill in the art.

The present invention is directed to DNA encoding a natural killer lytic associated protein selected from the group consisting of: (a) isolated DNA which encodes a human natural killer lyric associated protein; (b) isolated DNA which hybridizes to isolated DNA of (a) above and which encodes a human natural killer lyric associated protein; and (c) isolated DNA differing from the isolated DNAs of (a) and (b) above in codon sequence due to the degeneracy of the genetic code, and which encodes a human natural killer lytic associated protein. In one embodiment, the DNA has the sequence shown in SEQ ID No. 1. The DNA codes for natural killer lytic associated protein. In one embodiment, this protein has the amino acid sequence shown in SEQ ID No. 2.

The present invention is also directed to a plasmid adapted for expression in a recombinant cell containing the DNA of the present invention and regulatory elements necessary for expression of the DNA in the cell. Preferably, the plasmid contains the DNA shown in SEQ ID No. 1 and regulatory elements necessary for expression of the DNA in the cell.

The present invention is also directed to a host cell transfected with the vector of claim 4, said vector expressing a natural killer lytic associated protein. Generally, the host cell is selected from group consisting of bacterial cells, mammalian cells and insect cells. A representative example of a bacterial cell is *E. coil*. A representative example of a mammalian cell line is from a natural killer 3.3 cell line. A representative example of a insect cell is SF9.

The present invention is also directed to an isolated and purified natural killer lytic associated protein coded for by DNA selected from the group consisting of: (a) isolated DNA which encodes a human natural killer lytic associated protein (b) isolated DNA which hybridizes to isolated DNA of (a) above and which encodes a human natural killer lytic associated protein; and (c) isolated DNA differing from the isolated DNAs of (a) and (b) above in codon sequence due to the degeneracy of the genetic code, and which encodes a human natural killer lytic associated protein. Preferably, the isolated and purified natural killer lytic associated protein has the amino acid sequence shown in SEQ ID No. 2.

The present invention also encompasses a method of inhibiting expression of the DNA of claim 1, comprising the step of exposing said DNA to antisense oligonucleotides specific to said DNA sequence. Preferably, the antisense oligonucleotide has the sequence shown in SEQ ID No. 3 or SEQ ID No 4.

The present invention is also directed to a method of enhancing expression of the DNA of claim 1, comprising the step of exposing said DNA sequence to a cytokine. Preferably, the cytokine is selected from the group consisting of inteleukin-2, α interferon, β-interferon, 65-interferon and interleukin-12.

The present invention is also directed to a method for treating a pathophysiological state in an individual, comprising the step of administering to said individual a composition comprising a therapeutically effective dose of the plasmid of claim 4. Representative examples of pathophysiological state is selected from the group consisting of cancer and viral infections. Representative examples of cancers so treated include carcinoma and melanoma. Representative examples of viruses which may be treated by this method of the present invention include herpes simplex virus and hepatitis virus.

In one embodiment of the present invention, it would be therapeutically desirable to enhance the expression of the novel natural killer lytic associated protein of the present invention. Enhanced or increased expression of the natural killer lytic associated protein is desirable in treating specific diseases in which natural killer cells play a role in treating the disease the disease in vivo. Representative examples of pathophysiological states in which enhanced expression of the natural killer lytic associated protein is desirable include cancer and viral infections. Representative examples of cancer states in which enhanced expression of the natural killer lytic associated protein is desirable include renal carcinoma and melanoma. Representative examples of vital states in which enhanced expression of the natural killer lytic associated protein is desirable include herpes and hepatitis.

In another embodiment of the present invention, it would be therapeutically desirable to reduce, decrease or inhibit the expression of the novel natural killer lyric associated protein of the present invention. Representative examples of pathophysiological states in which reduced expression of the natural killer lyric associated protein is desirable include transplantation, i.e., graft rejection and autoimmune diseases. Representative examples of autoimmune diseases include systemic lupus erythematosus (SLE) and rheumatoid arthritis.

It is specifically contemplated that pharmaceutical compositions may be prepared using the novel natural killer lytic associated protein of the present invention. In such a case, the pharmaceutical composition comprises the novel natural killer lytic associated protein of the present invention and a pharmaceutically acceptable carrier. A person having ordinary skill in this art would readily be able to determine, without undue experimentation, the appropriate dosages and routes of administration of the novel protein of the present invention.

The following examples are given for the purpose of illustrating various embodiments of the invention and are not meant to limit the present invention in any fashion.

EXAMPLE 1

Referring to FIG. 1, a unique gene and its gene product have been identified that have a functional role in the natural killer and cytotoxic T cell lytic processes. The RNA expression of the novel gene of the present invention is largely limited to natural killer cells, cytotoxic T cells and macrophages, and is upregulated by cytokine activation. The functional role of the natural killer lytic associated protein has been demonstrated through, among other things, the ability of antisense oligonucleotides to the DNA encoding the natural killer lytic associated protein to selectively inhibit target cell lysis.

FIG. 1 shows a preferred embodiment of both the nucleotide sequence of the gene and the deduced amino acid sequence of the full length natural killer lytic associated protein. Double stranded DNA sequencing of natural killer lytic associated protein clones in the pBluescript plasmid (Stratagene) was done using Sequenase (United States Biochemical Corp.) according to manufacturer's protocol. Confirmation of the sequence of the 5', G-C rich region of natural killer lytic associated protein was performed subsequent to subcloning these fragments into the single stranded M13 phage. The oligonucleotides preferably used as primers to sequence natural killer lytic associated protein were:

M-13 universal primer
M-13 reverse primer
SK and KS primers
T3 and T7 primers
Oligo #194—5'-TGGAAGCTGTAATCACA-3'
Oligo #196—5'-TCTCATTGCTGGCATTG-3'
Oligo #213—5'-GTGGAGGTGGCTATGGA-3'
Oligo #217—5'-TGAGTGGCGGCATTCTC-3'
Oligo #218—5'-CAAGACAGTTTGTCCTC-3'
Oligo #223—5'-GGTTCATATGGGCACTT-3'
Oligo #A6—5'-GGCAGCTGATGGGCACC-3'
Oligo #S3—5'-GGACCCCGACTGCCGCTG-3'
Oligo #A3—5'-CAGCGGCAGTCGGGGTCC-3'
Oligo #S5—5'-TCCACATCGCTACATGCG-3'
Oligo #002—5'-AAGTCTGGGCCCTCTGT-3'
Oligo #001—5'-ACAGAGGGCCCAGACTT-3'
Oligo #S10—5'-GACAACGCAAGCACTCG-3'
Oligo #A9—5'-ATGCCTTCTCGGAGCCCAT-3'

Oligonucleotides corresponding to other stretches of the natural killer lytic associated protein DNA sequence may also be used as primers.

The 2.8 Kb cDNA for natural killer lytic associated protein, upon sequencing, revealed a single open reading frame of 1761 base pairs encoding a protein having 587 amino acid residues. The encoded natural killer lytic associated protein had a calculated molecular mass of 62,685 Da. In addition, the cDNA had a 189 base pair 5' and an 803 base pair 3' untranslated region. The cDNA contains a polyadenylation site and a poly A tail.

The first methionine in the amino acid sequence of FIG. 1 appears in the open reading frame of natural killer lytic associated protein and conforms to the consensus sequence for eukaryotic initiation sites and is presumed to be the initiation site and the initiation codon. M. Kozak, "Compilation and Analysis of Sequences Upstream from the Translational Start Site in Eukaryotic MRNAs," Nucleic Acid Res., 12:857–872 (1984). There is a potential nuclear targeting signal at amino acid position 341.

Sequence analysis at the DNA and protein level of the natural killer lytic associated protein using the Fasta and Tfasta programs within the GCG sequence analysis package and the BLAST network service at the National Center for Biotechnology Information (NCBI) revealed no extensive similarity between the natural killer lytic associated protein and any known genes or gene products, demonstrating the uniqueness of natural killer lytic associated protein. A comparison of the GCG protein database to defined protein motifs revealed a potential signal sequence for natural killer lytic associated protein between amino acid positions 45 and 46.

EXAMPLE 2

FIG. 2 shows the amino acid composition of the natural killer lytic associated protein. The sequence data was acquired using the MacVector sequence analysis software from International Biotechnologies International (IBI) and PC Gene. These programs were also used to identify further characteristics of the natural killer lytic associated protein.

EXAMPLE 3

Figure 3B:
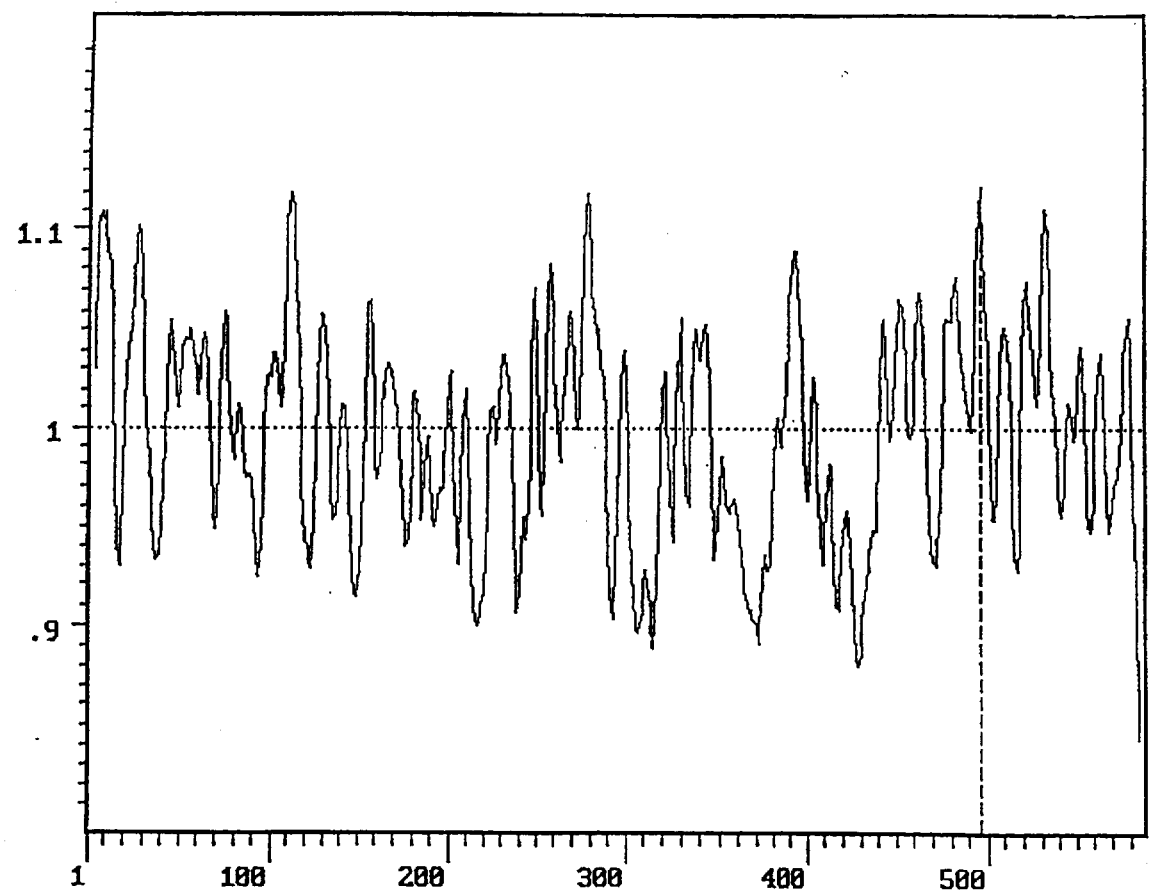
FIG. 3B shows a trace showing the flexibility of the natural killer lyric associated protein.
Figure 3C:
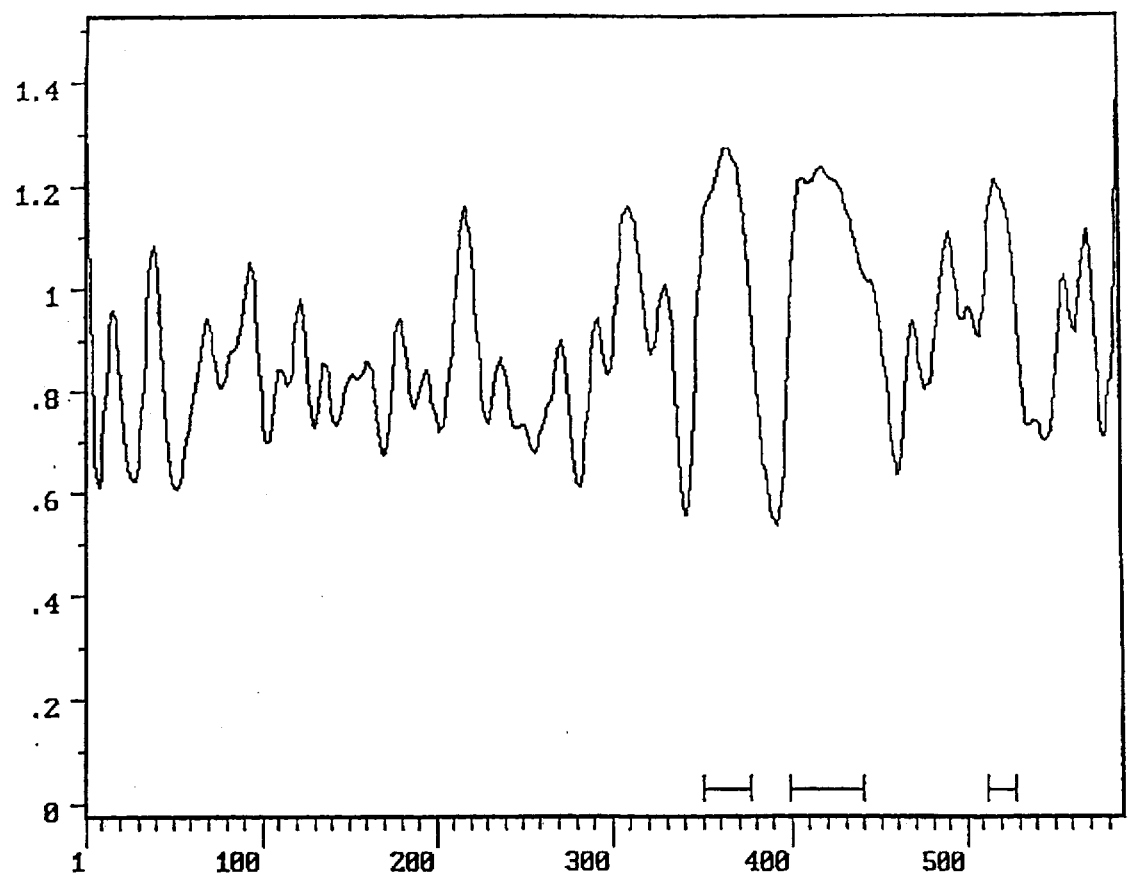
FIG. 3C shows the 3 predicted transmembrane helices of the natural killer lytic associated protein.
Figure 3D:
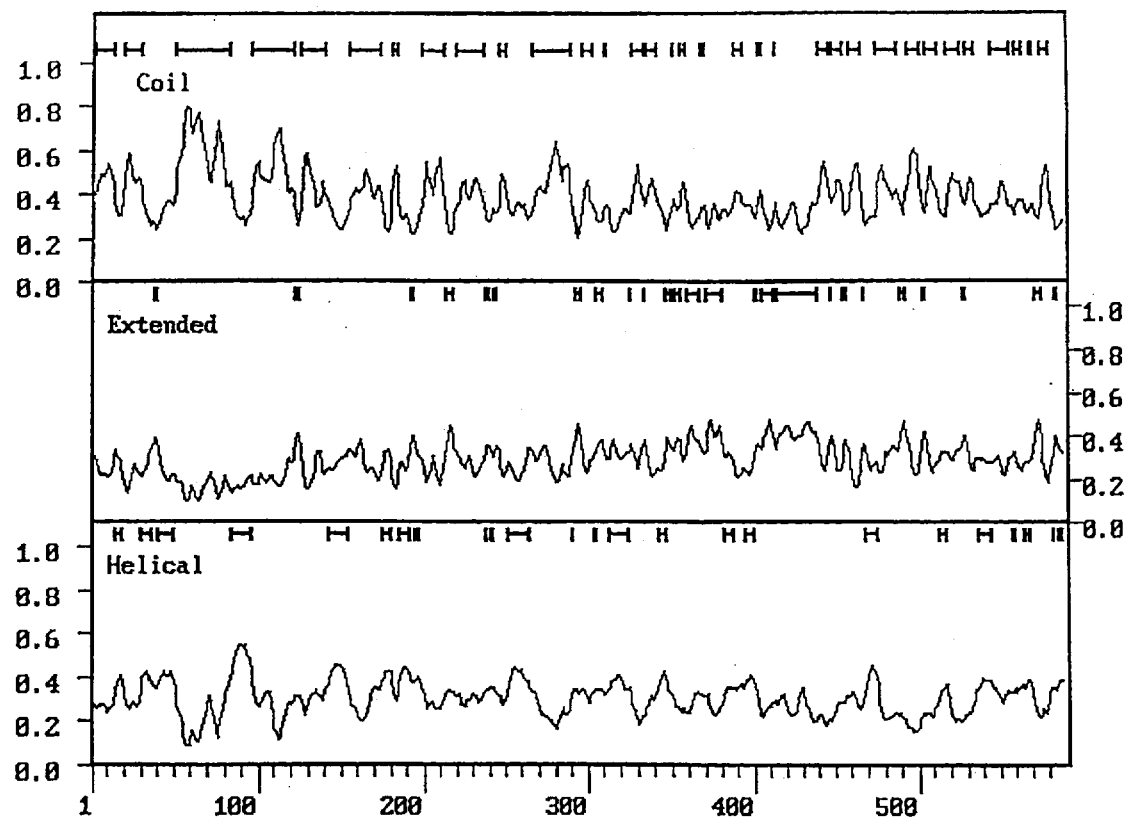
FIG. 3D shows a trace showing the secondary structure of the natural killer lytic associated protein.

FIG. 3A shows the hydrophilicity and antigenicity of the natural killer lytic associated protein. FIG. 3B shows the flexibility of the natural killer lyric associated protein. FIG. 3C shows the predicted transmembrane helices of the natural killer lyric associated protein. FIG. 3D illustrates the secondary structure of natural killer lyric associated protein.

While FIG. 1 shows the preferred composition of the cDNA for natural killer lyric associated protein, changes in the cDNA sequence may be made without causing protein sequence changes. For example, GCA and GCC both code for alanine. The 64 possible codons code for only 20 amino acids, and consequently most amino acids are encoded by more than one codon. Other cDNA sequences encoding the same protein are also part of the present invention and are included by the claims appended hereto.

The present invention is also directed to a recombinant expression vector containing a DNA sequence encoding natural killer lytic associated protein, in which the vector is capable of expressing natural killer lytic associated protein in a microorganism or cell culture. The preferred vector is pGEX-2T, which contains the glutathione S. transferase gene, plus a polylink for cloning of foreign genes to create a fusion protein for expression in E. coli. pGEX is available from Pharmacia, catalog No. 27-4801-01. The coding region of the natural killer lytic associated protein cDNA is cloned into Bam HI digested pGEX vector according to common laboratory cloning techniques well known to those skilled in the art. See, J. Sambrook, et at., Molecular Cloning, a Laboratory Manual, Cold Spring Harbor Laboratory Press (2d ed. 1989). Other vectors may be used, however, as is well known by those skilled in the art and discussed below. In the preferred embodiment, the natural killer lytic associated protein expressed by the vector has the amino acid sequence 1-587 set forth in FIG. 1. A preferred vector, pSKNKLAM-1 (phagemid) containing the novel DNA sequences of the present invention was deposited with the American Type Culture Collection on Feb. 17, 1995 and assigned ATCC accession number 97062.

EXAMPLE 4

The present invention is also directed to a microorganism transformed with a vector containing a DNA sequence encoding natural killer lytic associated protein. In a preferred embodiment, the transformed microorganism is E. coli. More specifically, the GST-natural killer lytic associated protein fusion protein described above may be expressed in BL21 plys S E. coli cells (obtainable from Novagen Inc.). Other E. coli cell lines may, of course, be used.

In the present invention, pGEX with an natural killer lyric associated protein insert may be cloned in BL21 plys S E. coli cells by electroporation (Bethesda Research Laboratories (BRL) protocol). A single colony may then be picked the following day of the LBAmp (Luria Broth Ampicillin) plate (from BRL). The transformed E. coil cells were then grown overnight in the TBAmp (Terrific Broth Ampicillin) medium (2.0 mls) at 37° C., shaking at 200 rpms. One milliliter of this overnight culture may then be used to inoculate 50 mls of TBAmp medium. The cells were grown to an OD550 of 0.4 and then inoculated with isopropylthio-$\beta$-D-galactoside (IPTG) to a final concentration of 0.3 millimole and grown for an additional three hours. Immediately before the addition of IPTG and after the 3 hour incubation, 1 ml and 0.4 ml samples of cells were taken, respectively. The cells were centrifuged (5 minutes at 10,000 rpms), the supernatant decanted, and the cells resuspended in 50 μls of SDS sample buffer. The remaining cell suspension (about 48 mls) was centrifuged for 10 minutes at 2,000 rpms. The cells were suspended in 1.0 ml of TNE-100 buffer (50 mM Tris-HCL pH-8.0; 100 mM NACl; 1 mM EDTA; 1 mM phenylmethylsulfonylfluoride (PMSF); and 1X protease inhibitor solution as described by Sambrook, et al., 1989). The cells and buffer were kept on ice. Lysozyme was added until a concentration of 1 mg/ml was reached, and the cells and buffer were kept on ice for an additional 5 minutes. A solution of 10% Triton X-100 was added to the cell solution that is 1/10 th of the cell solution by volume, and the solution was kept on ice for an additional 5 minutes. The cells were lysed by a freeze/thaw method (5 minutes at 70° C. and 5 minutes at 37° C.), which was performed twice. The lysed cells were then diluted 1/10 th by volume in PBS450+T (450 mM NACl; 20 mM sodium phosphate; 0.5 mM EDTA; 1% Triton X-100; 1 mM PMSF 1X protease inhibitors; and 1 mM DTT solution at pH 7.3). The 10 ml of lysed cell solution was put through a syringe and a 20 gauge needle at least 3 times to generate a uniform solution. The lysate was centrifuged for 10 minutes at 7,000 rpm in the cold and the supernatant (cell lysate) was transferred to a fresh tube. Then, 0.5 ml of glutathione-sepharose 4-B (from Pharmacia) equilibrated in PBS450+T was added to the cell lysate. This solution was incubated at 4° C. for at least 1 hour in a device that rocks the solution container. The resulting resin was centrifuged to the bottom of the container, and the supernatant was removed.

The resin was washed five times with 0.8 ml of PBS450+T. The resin was then washed with 0.8 ml of low glutathione elution buffer (50 mM Tris pH 8.0; 10 mM glutathione; 1 mM DTT; and 1X protease inhibitor solution) twice at 4° C. The GST-natural killer lytic associated protein was eluted using a high concentration glutathione elution buffer (100 mM). The elution fractions (0.8 ml each) were pooled, providing purified GST-natural killer lytic associated protein. GST can be cleaved from natural killer lytic associated protein by using the site specific protease thrombin (from Sigma Chemical Co.) at a concentration of 1 to 2 units/ml of reaction mixture, after a one hour incubation at 25° C. Cleavage was confirmed by polyacrylamide gel electrophoresis, which shows a 25 kDa band corresponding to GST and a 62 kDa band corresponding to natural killer lytic associated protein. In the preferred embodiment, the natural killer lytic associated protein has the amino acid sequence 1-587 set forth in FIG. 1.

The above protocol describes the isolation of soluble GST-natural killer lytic associated protein fusion protein in the bacterial cell extract. However, most GST-natural killer lytic associated protein is insoluble, and forms inclusion bodies in the bacterial cells. To isolate this To isolate this material, after the cell lysate supernatant is transferred to a new tube, it is re-centrifuged at 12,000 rpm for 25 minutes. The pellet, containing the inclusion bodies, is dissolved in 1-2 ml of 8M urea. This solubilized material was then dialyzed against PBS overnight at 4° C., followed by further purification using glutathione-sepharose 4-B as described above. By isolating GST-natural killer lytic associated protein from both the soluble and insoluble bacterial fractions, the yield of protein was maximized.

EXAMPLE 5

The present invention also includes a cell culture capable of expressing natural killer lytic associated protein, obtained by transforming a mammalian cell line with a vector containing a DNA sequence encoding natural killer lytic associated protein that is capable of being expressed in a transformed cell culture. While many cell lines could be utilized, in the preferred embodiment, the cell line is the natural killer 3.3 cell line. The transformed cell line may be produced using a number of protocols commonly used by those skilled in the art. The preferred method was adapted from *Methods in Molecular Biology*, Vol. 7, "Gene Transfer and Expression Protocols," edited by E. J. Murray, Humana Press, Clifton, N.J. The overall method involves using retroviruses to introduce the gene encoding the natural killer lytic associated protein into the human natural killer cell clone, natural killer 3.3. These viruses integrate into the host cell genome, thereby establishing cell lines that stably and continuously express the gene of interest.

Figure 4:
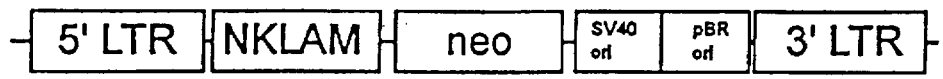
FIG. 4 shows a diagram showing the structure of the pZip/natural killer lyric associated protein/neo vector.

Specifically, the retroviral vector pZipneoSV(X), which contains the neomycin resistance gene (neo), was used. The neo gene provides a means for selecting cells expressing this vector by its ability to grow in the presence of the neomycin analog G418. A retroviral vector containing natural killer lytic associated protein was generated from pZipneoSV(X) by digesting the vector with restriction enzyme Bam H1 and ligating into it a Bam H1 fragment corresponding to the entire coding region of the natural killer lytic associated protein cDNA. Restriction digest analysis shows that the 5' end of the natural killer lytic associated protein fragment was oriented next to the 5' long-terminal repeat (LTR), which is necessary for the initiation of transcription. The neo gene and 3' LTR are 3' of natural killer lyric associated protein. This vector was designated pZip/natural killerlyric associated protein/neo (see FIG. 4). The vector pZip/natural killerlytic associated protein/neo was then transfected into the packaging cell line PA317 (available from ATCC, CRL 9078) by CaPO$_4$. Transfected PA317 cells were selected by growth in the presence of G418 (neomycin analog) (from Bethesda Research Laboratories) at a dose of 300 ug/ml, which kills nontransfected PA317 cells. Colonies of G418-resistant PA317 cells were expanded and tested for their ability to produce viruses containing the natural killer lytic associated protein gene. Supernatants containing viruses were collected and used to infect natural killer 3.3 cells.

EXAMPLE 6

Infection of the natural killer 3.3 cells was accomplished by incubating supernatants from PA317 cells producing retroviruses containing the natural killer lytic associated protein and neo genes with natural killer 3.3 cells in the presence of polybrene for 2 hours. Infected natural killer 3.3 cells were then selected by their ability to grow in G418-containing media. A visual microscopic count of the cells indicates their ability to grow. In the preferred embodiment, the natural killer lyric associated protein produced by this method has the amino acid sequence 1-587 set forth in FIG. 1.

Natural killer 3.3 can also be transfected with mammalian expression vectors by electroporation. Selection of expression and integration of the plasmids can be performed as described above. Vectors, such as pCDNA3 and pCEP4, can be used for this purpose. Here, the natural killer lytic associated gene would be driven by the cytomegalovirus (CMV) promoter, which has been shown to work in natural killer 3.3 and in many other mammalian cells. These plasmids also contain the neo or hygromycin resistance genes so that selection of plasmid-containing cells can be performed by growing cells in G418 or hygromycin, respectively, as described above.

The specific vectors and methods disclosed above are suitable for use in host cells over a wide range of prokaryotic and eukaryotic organisms. In general, prokaryotes are preferred for cloning of DNA sequences in constructing the vectors useful in the invention. The *E. coli* strain mentioned above is preferred in the present invention. Other microbial strains that may be used include, but are not limited to, *E. coil* B and *E.coli* X1776 (ATCC No. 31537). Other prokaryotes may also be used for expression. The above *E. coli* strains, *E. coli* W3110 (F-,λ-, prototropic, ATCC No. 27325), bacilli such as *Bacillus subtilus*, and other enterobacteriaceae such as *Salmonella typhimurium* or *Serratia marcesens*, and various pseudomonus species may be used.

Generally, plasmid vectors containing replicon and control sequences which are derived from species compatible with the host cell may be used in connection with the hosts. Details concerning such microbial promoters have been published, enabling a skilled worker to ligate them functionally with plasmid vectors. See, for example, Siebenlist, et al., *Cell*, 20:269 (1980). A preferred vector in the present invention, as stated above, is pGEX-2T.

Eukaryotic microbes, such as yeast cultures, may also be used as hosts. For example, *Saccharomyces cerevisiae* is commonly used with the plasmid YRp7. Stinchcomb, et at., *Nature*, 282:39 (1979); Kingsman, et al., *Gene*, 7:141 (1979). Suitable promoting sequences in yeast vectors include the vectors for 3-phosphoglycerate kinase or other glycolytic enzymes. Any plasmid vector containing yeast-compatible promoter, origin of replication and termination sequences may be suitable.

Mammalian cell lines have been described above as hosts, and in a preferred embodiment is the human natural killer3.3 cell line. Any cell culture is workable, however, whether from vertebrate or invertebrate culture. Other useful host cell lines include, but are not limited to, VERO cells, HeLa cells, Chinese hamster ovary CH) cell lines, and W138, BHK, COS-7, and MDCK cell lines.

EXAMPLE 7

Another aspect of the present invention is a method of preparing a DNA isolate comprising a DNA sequence encoding natural killer lytic associated protein. While various methods for preparing DNA isolates are known in the art, the following method was initially and is a preferred method of this invention. First, an interferon-βstimulated natural killer 3.3 cDNA library was prepared. To prepare the cDNA library, RNA was extracted from interferon-β stimulated natural killer 3.3 cells using guanidinium isothiocyanate. PolyA mRNA was isolated by oligo dT sepharose chromatography, and polyA RNA molecules were used as templates for the synthesis of DNA:RNA hybrids using random primers (from Stratagene). Random primers were chosen so that even if many cDNAs were not full length, overlapping clones may be pulled out to obtain the entire sequence. RNA was removed by NaOH denaturation and double stranded DNA was synthesized. EcoRI linkers (from Stratagene) are added to the cDNAs size selected to greater than 500 base pairs and ligated to λ ZAP II vector arms (from Stratagene). The DNA is packaged within the λ ZAP II phage particles and used to infect XLI-B *E. coli* cells. To select genes expressed at elevated levels in interferon-β-stimulated natural killer 3.3 cells, differential screening of 1×10⁶ phages containing the cDNA inserts was performed. ³²P-labeled cDNA synthesized from polyA mRNA from interferon-β and non-stimulated natural killer 3.3 cells were used as probes. After three rounds of screening, phages which hybridize strongly to cDNA from interferon-β treated natural killer 3.3 cells, but weakly or not at all to RNA from non-stimulated natural killer 3.3 cells, were identified and purified.

A combination of DNA sequencing using the GenBank, European Molecular Biology Laboratory (EMBL) and Protein Identification Resource (PIR)-Protein databases and Northern blot analysis was used to determine the nature of the cDNAs in the phages. The cDNA inserts range in size from 0.8 kb to 3.5 kb. Of the 56 cDNAs which have been partially sequenced (150–300 bps), 46 encode genes that appear to be unique and previously undescribed. Ten encode known genes. These include the HLA-DP MHC class II molecule, which is known to be expressed at elevated levels in activated natural killer cells. Identifying this gene in the library assures the quality of the cDNA library. In addition, a gene with 100% homology to heat shock cognate protein 70 (hsc70) was found when the method was properly performed. Northern blot analysis showed that hsc70 mRNA was strongly upregulated by cytokines IL-2 and interferon in natural killer 3.3 cells.

Clones with unique sequences may be used as probes to screen RNA from IL-2, interferon-β, and unstimulated, "starved" natural killer 3.3 cells by Northern blot analysis. Defining transcripts expressed at elevated levels in both IL-2 and interferon-β treated natural killer 3.3 cells increases the chances of obtaining genes specific to lytic activity. Northern blots of the novel cDNA clones was then used to identify the gene encoding the natural killer lytic associated protein of the present invention. Its RNA transcript size was approximately 2.8 Kb and its level of expression increased 8–10 fold in natural killer 3.3 cells treated with interferon-β and 5 fold in natural killer 3.3 cells treated with IL-2 relative to non-stimulated cells (See FIG. 5).

The original natural killer lytic associated protein cDNA clone identified in this library was 1.8 Kb, and therefore not full length. Screening of this cDNA library to pull out the remaining sequence of natural killer lytic associated protein was unsuccessful. Therefore, a second cDNA library was created using the most 5' and 3' sequences of natural killer lyric associated protein as primers for cDNA synthesis. From this new library, clones containing the remaining 5' and 3' sequences of natural killer lyric associated protein were identified and sequenced.

Figure 5:
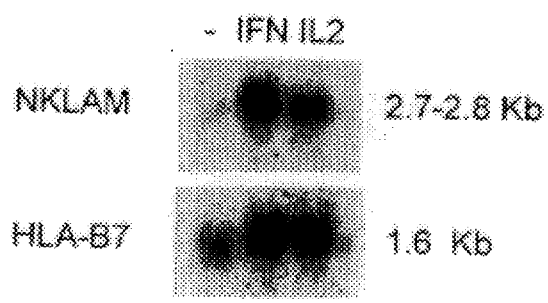
FIG. 5 illustrates the levels of expression of natural killer lytic associated protein by natural killer 3.3 cells in the presence and absence of the cytokines, IL-2 and interferon-β.
Figure 6:
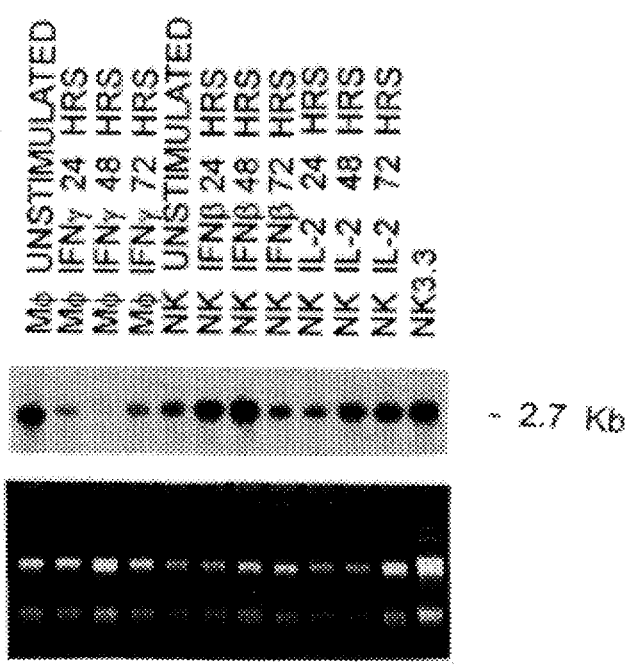
FIG. 6 shows the increased expression of natural killer lyric associated protein in peripheral blood natural killer cells after IL-2 and interferon stimulation, and constitutive expression by macrophages.

FIG. 5 shows the results of incubating natural killer 3.3 cells with no cytokines (-), IL-2 (20 U/ml), and interferon-β (5000 U/ml) for 4 hours and then loading 5 ug of total cellular RNA in each lane of a 1.5% agarose/6% formaldehyde gel. The RNA is then electrophoresed, blotted and probed with the original 1.8 Kb cDNA clone encoding the natural killer lyric associated protein to show the respective levels of expression of natural killer lytic associated protein in each lane.

In the preferred embodiment, cDNA encoding the natural killer lyric associated protein was used as a probe for Northern blot analysis and has the nucleotide sequence 750–2800 as set forth in FIG. 1. This was superior to the full length clone because the high G-C rich content of the 5' end of natural killer lytic associated protein generates nonspecific binding to other RNA species.

The method described above was utilized initially to isolate and characterize natural killer lyric associated protein from an interferon-β stimulated natural killer 3.3 cDNA library. Now that the entire coding region of the gene has been sequenced, the polymerase chain reaction (PCR) technique may be used to isolate natural killer lytic associated protein from a cDNA library. In addition to the natural killer 3.3 cDNA library, a library generated from cytokine stimulated peripheral blood natural killer cells, CTL or macrophages could also be used, since the natural killer lytic associated protein is expressed in these cells. Oligonucleotide primers corresponding to the 5' and 3' ends of the coding sequence of natural killer lytic associated protein is generated, and used as PCR primers to amplify the natural killer lytic associated protein cDNA in the library. A TA cloning kit from Invitrogen, or similar system, would then be used to clone the PCR product (natural killer lytic associated protein) directly from the PCR reaction into a vector for transforming bacteria, as described more fully in Ausubel, et al., *Current Protocols in Molecular Biology*, Vol. 2, Unit 15, Greene Pub. Associates (1992). However, it may be difficult to find the full length sequence of natural killer lytic associated protein in a standard cDNA library. The 5' end of natural killer lytic associated protein, being extremely G-C rich, has a lot of secondary structure (hairpin loop structures), which impairs the ability of the reverse transcriptase enzyme to read through.

EXAMPLE 8

The present invention also involves a method of preparing natural killer lytic associated protein. While a variety of techniques may be practiced by those skilled in the art, a preferred method, as described above in detail, uses recombinant expression vectors. Generally, the method involves adding a recombinant vector containing a DNA sequence encoding natural killer lytic associated protein to a culture in vitro in order to either transform microorganisms or transform cells. The vectors used are capable of expressing natural killer lytic associated protein in a host-vector system. Then, the recombinant expression vectors are allowed to encode natural killer lytic associated protein for a desired time period or until a desired quantity of natural killer lytic associated protein is produced. Finally, the natural killer lytic associated protein is isolated according to the procedure set out above. Preferably, the DNA sequence encoding natural killer lytic associated protein encodes the amino acid sequence 1-587 as set forth in FIG. 1. In addition, the preferred microorganism is an *E. coli* microorganism. The most preferred microorganism is BL21 plys S *E. coil*. When cells are used, the preferred method uses mammalian cell lines, and most preferably, a human natural killer 3.3 cell line.

EXAMPLE 9

Another aspect of the present invention involves methods for enhancing and inhibiting expression of a DNA sequence encoding natural killer lytic associated protein. For in vitro inhibition of natural killer 3.3 lytic activity, antisense oligonucleotides corresponding to various regions of natural killer lyric associated protein's open reading frame were synthesized on a cyclone plus DNA synthesizer. For controls, oligonucleotides corresponding to the sense strand of natural killer lytic associated protein were used. Prior to addition of natural killer lyric associated protein oligonucleotides, the natural killer 3.3 cells were cultured 3 days in natural killer media (RPMI 1640, 10% FCS, 15% Lymphocult-T from Biotest Diagnostics, and 1% glutamine) and then another 24 hours in tumor cell media (TCM) (RPMI 1640, 10% FCS, and 1% glutamine). Other reagents are obtained from Gibco Life Technologies.

90,000 natural killer 3.3 cells in 100 µl of tumor cell media (containing FCS heated to 65° C. to remove DNase activity) were placed into a well of a 96 well plate. Natural killer lytic associated protein sense or antisense oligonucleotide was then added to a given concentration and the cells were incubated for an additional 1-2 hours. The preferred concentration of oligonucleotide is 75 µM. From about 50 to about 100 µM concentrations could be used. IL-2 was added for a final concentration of 10 units/ml, and the cells were incubated for an additional 6 hours. At this point, the cells may be tested for cytolytic activity against K562, an erythroleukemia cell line, using a 4 hour $^{51}$Cr release assay.

EXAMPLE 10

For in vitro inhibition of peripheral blood natural killer lyric activity, peripheral blood lymphocytes (PBL) were isolated from a healthy donor by centrifugation on a Ficoll-Hypaque density gradient and by adherence to Ti75 tissue culture flask to remove monocytes. The majority of T cells were removed by E-rosetting. An natural killer enriched population of PBL was then obtained by negative selection using monoclonal antibodies specific to CD19 (to remove B cells), CD14 (to remove monocytes) and CD3 (to remove T cells), followed by anti-mouse IgG magnetic beads. The same oligonucleotides used with the natural killer 3.3 cells were used here. Following the purification of peripheral blood natural killer cells, the cells were cultured in tumor cell media containing 100 units/ml IL-2 for 24 hours. The cells were then removed from this medium and resuspended in tumor cell media (with FCS heated to 65° C.) at a concentration of 150,000 cells/ml to $1.2 \times 10^6$ cells/ml depending on the activity of the isolated natural killer cells. 100 µl of the cell suspension was added to a well of a 96 well plate. Oligonucleotides to natural killer lytic associated protein (sense or antisense) were added to a desired concentration (10–100 µM). The preferred concentration is 75 gM. A range of 50–100 µM is acceptable. The cells were then incubated for 2 hours at 37° C. in 5% $CO_2$, and then IL-2 was added to a concentration of 100 units/mi. The cells are incubated for an additional 6-7 hours. The cells may then be assayed for lytic activity using the $^{51}$Cr release assay and K562 and JY cells as targets. The treated cells will regain lytic activity upon removal of the antisense oligonucleotide.

The erythro-leukemia cell line K562 is highly susceptible to the cytolytic activity of natural killer cells and is the most widely used cell line for assessing natural killer activity. JY is an Epstein-Barr virus transformed B lymphoblastoid cell line, which is insensitive to natural killer lysis but is sensitive to lysis mediated by IL-2 stimulated natural killer cells and by CTL that have been generated to specifically recognize the HLA molecules expressed by them.

Controls for the antisense studies include natural killer cells which are kept in TCM ±IL-2 during the course of the study. The IL-2 was added to the cells at the same time as IL-2 was added to cells containing the oligonucleotides. The unstimulated cells remain without IL-2 for 24 hours prior to addition of oligonucleotides and for the subsequent approximately 8 hours prior to $^{51}$Cr release assay.

The cytolytic activity of untreated, antisense-oligonucleotide treated, and gene transduced natural killer cells and CTL was assessed using a standard 4 hour chromium ($^{51}$Cr) release assay as described in I. Kornbluth, "Evidence for the Role of Class I and Class II HLA Antigens in the Lytic Function of a Cloned Line of Human Natural Killer Cells,"*J. Immunol.*, 134:728 (1985). Briefly, 3000 $^{51}$Cr-labeled targets were incubated with effectors (natural killer or CTL) at 37° C. for 4 hours in round-bottom microtiter plate wells in a final volume of 0.2 ml RPMI 1640 plus 10% FCS. All conditions were set up in triplicate. Lysis was measured at effector:target (E:T) cell ratios ranging from 30:1 to 2:1. After 4 hours, 0.1 ml volumes of supernatant from each well were assessed for $51^{Cr}$ using a gamma counter. The percent specific lysis of targets was then calculated from each ratio.

Figure 8:
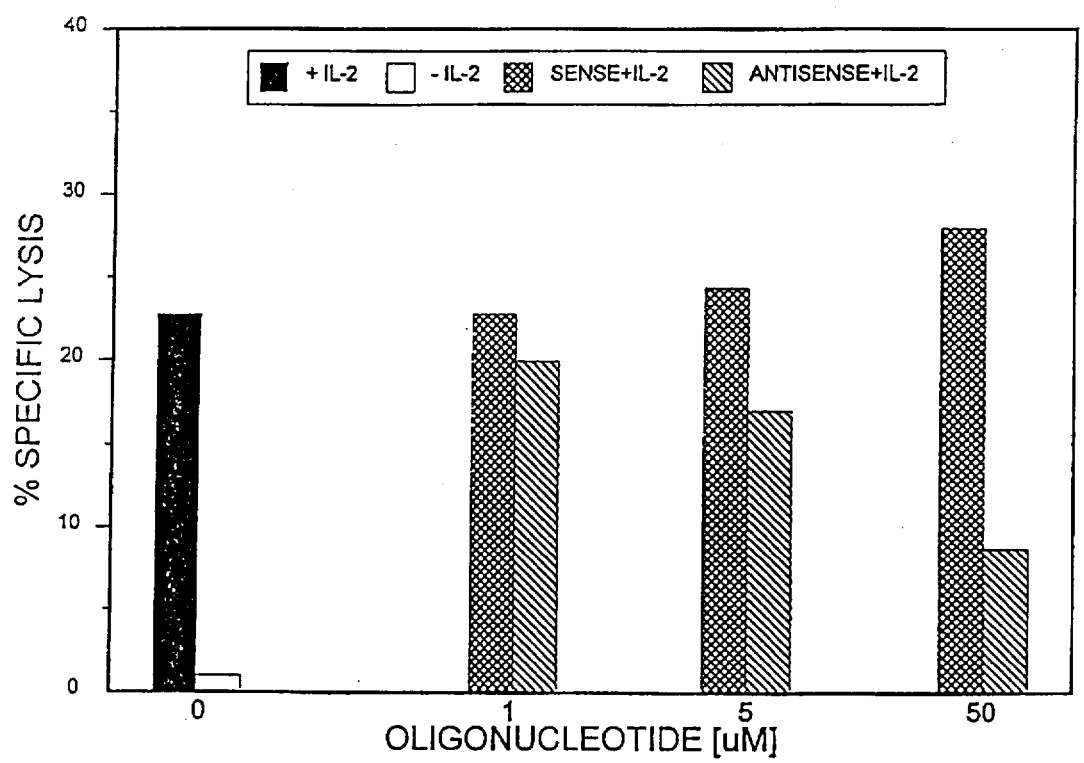
FIG. 8 shows the increasing inhibition of natural killer cytotoxicity when natural killer 3.3 cells are exposed to increasing concentrations of antisense oligonucleotides directed against the gene encoding the natural killer lytic associated protein.
Figure 9:
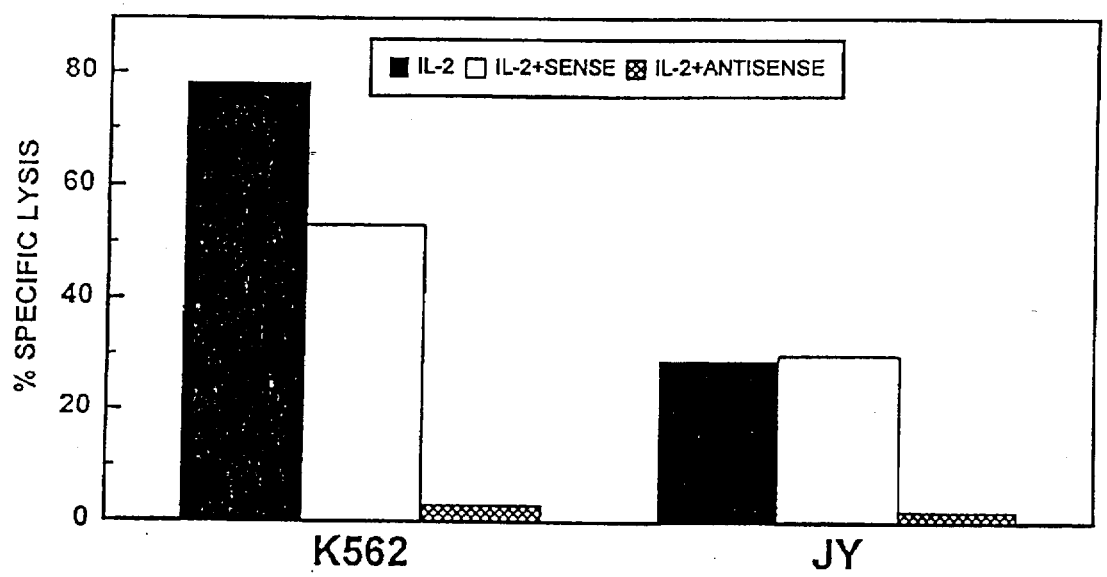
FIG. 9 shows inhibition of peripheral blood natural killer lytic activity, both IL-2 induced and basal, by treatment of cells with antisense oligonucleotides directed against the gene encoding the natural killer lytic associated protein.
Figure 10:
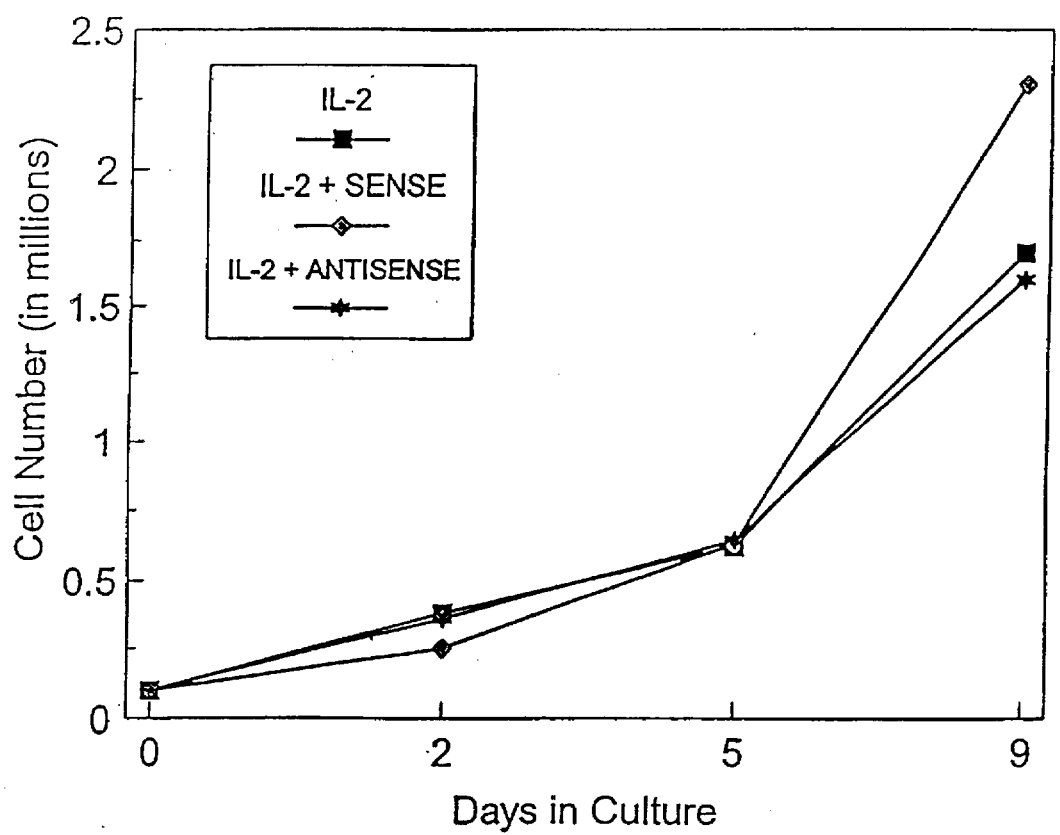
FIG. 10 shows that antisense oligonucleotides directed against the gene encoding the natural killer lyric associated protein do not inhibit the IL-2 dependent proliferation of natural killer 3.3 cells.

FIG. 8 shows the increasing inhibition of natural killer 3.3 natural killer lytic activity as the concentration of antisense oligonucleotides was increased. FIG. 9 shows the ability of antisense oligonucleotides directed to the gene encoding the natural killer lytic associated protein to inhibit the peripheral blood natural killer cell lytic function against the natural killer sensitive cell line K562 and the natural killer resistant, LAK sensitive cell line JY. This demonstrates inhibition of both IL-2 induced and basal natural killer lytic activity. This inhibition was specific for cytotoxic activity. As shown in FIG. 10, natural killer lytic associated protein antisense oligonucleotides did not inhibit the IL-2 dependent proliferation of natural killer 3.3 cells.

EXAMPLE 11

The method of enhancing expression of a DNA sequence encoding natural killer lytic associated protein comprises exposing cells expressing this DNA sequence to a cytokine or other suitable agents. In addition to the cytokines IL-2, IL-12 and the interferons, a variety of other agents have been shown to stimulate natural killer activity. The HLA-A locus specific monoclonal antibody 131 augments natural killer 3.3 cytolytic activity and natural killer lytic associated protein RNA expression. IL-4 treatment also increases natural killer lytic associated protein expression in natural killer 3.3 cells. Crosslinking of cell surface CD16 using anti-CD16 antibody coupled to Sepharose beads or addition of a second antibody (goat anti-mouse IgG) or by stimulating CD16 with aggregated IgG or immune complexes also activates natural killer cells and may induce natural killer lytic associated protein expression. Additional cytokines that may increase natural killer activity either alone or in combination are IL-6, IL-7, and tumor necrosis factor.

One preferred embodiment for augmenting natural killer activity involves culturing natural killer 3.3 cells for 18 hours in culture medium (TCM) and then stimulating for specified time periods with 5000 units/ml interferon-β or 10-100U IL-2. About $5-10 \times 10^6$ cells were then harvested at certain time points and immediately solubilized for extraction of RNA as described above. FIG. 11 shows the results of a procedure as follows: 5 ug of total RNA for each time point shown was electrophoresed on a 1.5% agarose/6% formaldehyde gel, blotted and probed with the $^{32}p$ labeled natural killer lyric associated protein cDNA clone. The blot was stripped and reprobed with a probe for ribosomal protein RPS3 (probe obtained from ATCC) as a control. Preferably, the cytokine used is interleukin-2, interferons (α, β, γ), or interleukin-12. The most preferred cytokines are IL-2 and interferon-β.

EXAMPLE 12

Figure 12:
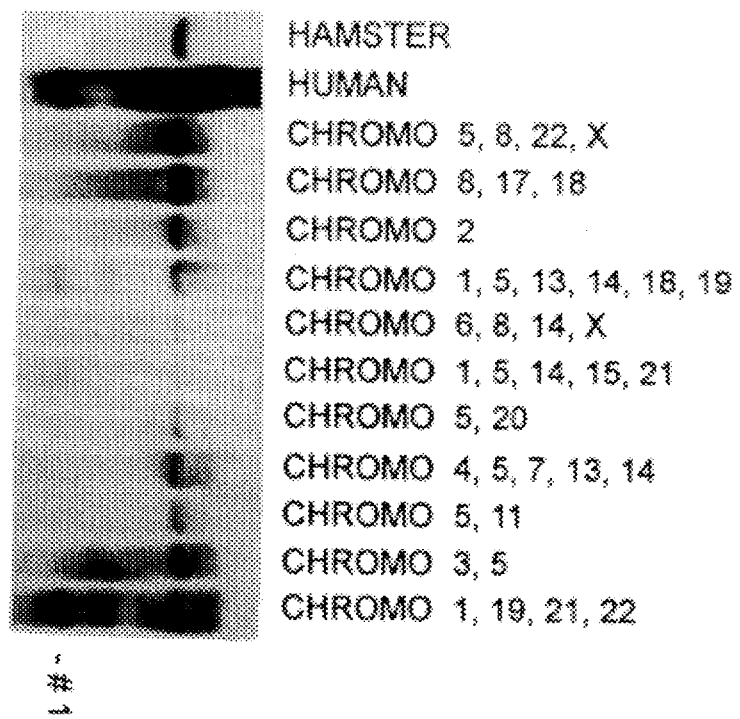
FIG. 12 shows the mapping of the natural killer lytic associated gene to human chromosome 1.

FIG. 12 shows the mapping of natural killer lyric associated protein to human chromosome 1 by Southern blot analysis of DNA from a series of mouse x human and hamster×human hybrid cell lines containing different complements of human chromosomes.

The natural killer lytic associated protein and the gene encoding this protein described above may be implemented in medical treatments for cancers; viruses; bacteria such as *Listeria monocytogenes, Chlamydia trachomatis,* Mycobacterium, Shigella, and Legionella pneumophila; fungi such as *Cryptococcus neoformans, Paracoccidiodes brasiliensis,* and *Coccidioides immitis*; yeasts such as *Candida albicans*; and protozoal parasites such as Leishmania, Toxoplasma, and Plasmodium.

A general treatment strategy for cancer is one of gene therapy. Tumor-infiltrating lymphocytes, comprising cytotoxic T cells and natural killer cells, are isolated after the surgical removal of the tumor, expanded in vitro in the presence of IL-2 and then genetically modified to express large amounts of natural killer lytic associated protein. This could be done by retroviral-mediated transduction of natural killer lytic associated protein into the TIL cells (as described above in detail). This method has been successfully used by others to modify tumor-infiltrating lymphocyte cells and then reintroduce them into patients. Other methods of gene transduction, using other vectors such as adeno-associated viruses or adenoviruses are also possible. In cases where tumor-infiltrating lymphocyte cells are unavailable (inoperable tumor sites or in cases of vital or microbial diseases), one may obtain T lymphocytes and natural killer cells from the peripheral blood of these individuals, expand these cells with IL-2 in vitro, infect them with an natural killer lytic associated protein-containing retroviral vector, and then reinfuse the cells.

The overall goal is to generate highly cytolytically active cells that can be introduced into patients and be therapeutically beneficial without major side effects, such as those seen when patients were treated with IL-2 to maintain the cytolytic activity of the tumor-infiltrating lymphocyte cells. This protocol is adapted from the one described by Steven A. Rosenberg, M.D., Ph.D. in *Human Gene Therapy*, 1:443–462, (1990). Preferably, the natural killer lytic associated protein expressed as a result of this method has the amino acid sequence 1-587 as set forth is FIG. 1.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. DNA encoding a natural killer lytic associated protein, wherein said DNA has the sequence shown in SEQ ID No. 1.

2. The DNA of claim 1, wherein said natural killer lytic associated protein has the amino acid sequence shown in SEQ ID No. 2.

3. A vector capable of expressing the DNA of claim 1 in a recombinant cell wherein said vector comprises regulatory elements operably linked to said DNA.

4. The vector of claim 3, wherein said DNA encodes a natural killer lytic associated protein having the amino acid sequence shown in SEQ ID No. 2.

5. A host cell transfected with the vector of claim 3, said vector expressing a natural killer lytic associated protein.

6. The host cell of claim 5, wherein said cell is selected from group consisting of bacterial cells, mammalian cells and insect cells.

7. The host cell of claim 6, wherein said bacterial cell is E. coli.

8. The host cell of claim 6, wherein said mammalian cell line is from a natural killer cell line.

9. The host cell of claim 6, (wherein said insect cell line is a SF9 cell line.

* * * * *